US009920085B2

(12) United States Patent
Hanson

(10) Patent No.: US 9,920,085 B2
(45) Date of Patent: Mar. 20, 2018

(54) BORONIC ACID CONJUGATES OF OLIGONUCLEOTIDE ANALOGUES

(71) Applicant: Sarepta Therapeutics, Inc., Corvallis, OR (US)

(72) Inventor: Gunnar J. Hanson, Bothell, WA (US)

(73) Assignee: SAREPTA THERAPEUTICS, INC., Cambridge, MA (US)

( * ) Notice: Subject to any disclaimer, the term of this patent is extended or adjusted under 35 U.S.C. 154(b) by 223 days.

(21) Appl. No.: 14/386,720

(22) PCT Filed: Mar. 7, 2013

(86) PCT No.: PCT/US2013/029684
§ 371 (c)(1),
(2) Date: Sep. 19, 2014

(87) PCT Pub. No.: WO2013/142087
PCT Pub. Date: Sep. 26, 2013

(65) Prior Publication Data
US 2015/0080340 A1    Mar. 19, 2015

Related U.S. Application Data

(60) Provisional application No. 61/613,385, filed on Mar. 20, 2012.

(51) Int. Cl.
C07F 9/6596    (2006.01)
C07F 9/6558    (2006.01)
C12N 15/113   (2010.01)

(52) U.S. Cl.
CPC ........ *C07F 9/6596* (2013.01); *C07F 9/65583* (2013.01); *C12N 15/113* (2013.01); *C12N 2310/31* (2013.01); *C12N 2310/3233* (2013.01); *C12N 2310/331* (2013.01); *C12N 2310/351* (2013.01)

(58) Field of Classification Search
CPC ... C07F 9/6596; C07F 9/65583; C12N 15/113
See application file for complete search history.

(56) References Cited

U.S. PATENT DOCUMENTS

| 6,030,954 | A | 2/2000 | Wu et al. |
|---|---|---|---|
| 6,548,651 | B1 | 4/2003 | Nielsen et al. |
| 7,402,574 | B2 | 7/2008 | Iversen et al. |
| 7,790,694 | B2 | 9/2010 | Geller et al. |
| 8,969,551 | B2 | 3/2015 | Ueda |
| 2004/0110296 | A1 | 6/2004 | Vargeese et al. |
| 2006/0104989 | A1 | 5/2006 | Edwards et al. |
| 2007/0082336 | A1 | 4/2007 | Johnsson et al. |
| 2008/0160225 | A1* | 7/2008 | Lowe ................ G01N 33/5308 428/29 |
| 2010/0105865 | A1 | 4/2010 | Telford et al. |
| 2010/0137408 | A1 | 6/2010 | Geller et al. |
| 2010/0234280 | A1 | 9/2010 | Geller et al. |
| 2013/0289091 | A1 | 10/2013 | Geller et al. |
| 2014/0213737 | A1 | 7/2014 | Weller et al. |

FOREIGN PATENT DOCUMENTS

| JP | 2002-167441 A | 6/2002 |
|---|---|---|
| JP | 2002-540113 A | 11/2002 |
| JP | 2003-521680 A | 7/2003 |
| JP | 2008-513012 A | 5/2008 |
| JP | 2010-505741 A | 2/2010 |
| JP | 2011-217751 A | 11/2011 |
| WO | 97/40854 A2 | 11/1997 |
| WO | 2000/056740 A1 | 9/2000 |
| WO | 01/49775 A2 | 7/2001 |
| WO | 2001/051689 A1 | 7/2001 |
| WO | 01/76636 A2 | 10/2001 |
| WO | 02/079467 A2 | 10/2002 |
| WO | 02/094250 A3 | 11/2002 |
| WO | 2003/078583 A2 | 9/2003 |
| WO | 2004/097017 A2 | 11/2004 |
| WO | 2006/033933 A2 | 3/2006 |
| WO | 2006/085973 A2 | 8/2006 |
| WO | 2006/121951 A2 | 11/2006 |
| WO | 2011/150408 A2 | 12/2011 |
| WO | WO 2011/150408 A1 * | 12/2011 ................ C07F 9/24 |

OTHER PUBLICATIONS

Agrawal et al., "Antisense therapeutics: is it as simple as complementary base recognition?," *Molecular Med. Today* 6:72-81, 2000.
Agrawal, "Antisense oligonucleotides: towards clinical trials," *Tibtech* 14(10):376-387, 1996.
Bramhill, "Bacterial Cell Division," *Annu Rev Cell Dev Biol* 13:395-424, 1997.
Crooke, Antisense Research and Applications, ed. Springer, 1999, Chapter 1, "Basic Principles of Antisense Therapeutics," pp. 1-50.
Deere et al., "Antisense Phosphorodiamidate Morpholino Oligomer Length and Target Position Effects on Gene-Specific Inhibition in *Escherichia coli*," *Antimicrobial Agents and Chemotherapy* 49(1):249-255, Jan. 2005.
Donachie, "The Cell Cycle of *Escherichia coli*," *Annu. Rev. Microbiol.* 47:199-230, 1993.
Dryselius et al., "The Translation Start Codon Region Is Sensitive to Antisense PNA Inhibition in *Escherichia coli,*" *Oligonucleotides* 13:427-433, 2003.
Galloway et al., "A mutant of *Escherichia coli* defective in the first step of endotoxin biosynthesis," *J. Biol. Chem.* 265(11):6394-6402, 1990.
Geller et al., "Antisense Antibacterial Method and Compound," Office Action, dated Sep. 29, 2010, U.S. Appl. No. 11/173,847, 25 pages.
Geller et al., "Antisense phosphorodiamidate morpholino oligomer inhibits viability of *Escherichia coli* in pure culture and in mouse peritonitis," *Journal of Antimicrobial Chemotherapy* 55:938-988, 2005.

(Continued)

*Primary Examiner* — Joseph R Kosack
(74) *Attorney, Agent, or Firm* — Brian C. Trinque; Lathrop Gage LLP

(57) ABSTRACT

Oligonucleotide analogs comprising boronic acid and/or boronic ester moieties are provided. The disclosed compounds are useful for the treatment of diseases where inhibition of protein expression or correction of aberrant mRNA splice products produces beneficial therapeutic effects.

22 Claims, 2 Drawing Sheets

(56) References Cited

OTHER PUBLICATIONS

Geller et al., "Inhibition of Gene Expression in *Escherichia coli* by Antisense Phosphorodiamidate Morpholino Oligomers," *Antimicrobial Agents and Chemotherapy* 47(10):3233-3239, Oct. 2003.
Geller et al., "Translocation of Pro-OmpA across Inner Membrane Vesicles of *Escherichia coli* Occurs in Two Consecutive Energetically Distinct Steps," *The Journal of Biological Chemistry* 264(28):16465-16469, 1989.
GenBank Accession No. AF074613, retrieved Jul. 15, 2010, from http//www.ncbi.nlm.nih.gov/nuccore/3822114. 45 pages.
GenBank Accession No. AJ007716, retrieved Jul. 15, 2010, from http//www.ncbi.nlm.nih.gov/nuccore/4775309. 4 pages.
GenBank Accession No. X97542.1, retrieved Jul. 15, 2010, from http//www.ncbi.nlm.nih.gov/nuccore/2244635. 4 pages.
GenBank Accession No. Y11275.1, retrieved Jul. 15, 2010, from http//www.ncbi.nlm.nih.gov/nuccore/4127812. 4 pages.
GenBank Accession No. AB011549, retrieved Jul. 15, 2010, from http//www.ncbi.nlm.nih.gov/nuccore/4589740. 35 pages.
Gerdes et al., "Experimental Determination and System Level Analysis of Essential Genes in *Escherichia coli* MG1655," *Journal of Bacteriology* 185(19):5673-5684, Oct. 2003.
Gilbert et al., "Sieve analysis: methods for assessing from vaccine trial data how vaccine efficacy varies with genotypic and phenotypic pathogen variation," *J Clinical Epidemiology* 54:68-85, 2001.
Good et al., "Antisense PNA Effects in *Escherichia coli* are limited by the outer-membrane LPS layer," *Microbiology* 149(Pt 10):2665-2670, 2000.
Good et al., "Bactericidal antisense effects of peptide-PNA conjugates," *Nature Biotechnology* 19(4):360-364, Apr. 2001.
Good et al., "Inhibition of translation and bacterial growth by peptide nucleic acid targeted to ribosomal RNA," *Proc. Natl. Acad. Sci. USA* 95(5):2073-2076, 1998.
Greenberg et al., "Antisense Phosphorodiamidate Morpholino Oligmers Targeted to an Essential Gene Inhibit Burkholderia cepacia Complex," *The Journal of Infectious Diseases* 201(12):1822-1830, Jun. 2010.
Hale et al., "Recruitment of ZipA to the Septal Ring of *Escherichia coli* is Dependent on FtsZ and Independent of FtsA," *Journal of Bacteriology* 181(1):167-176, Jan. 1999.
Hunt et al., "Identification of Burkholderia cenocepacia Genes Required for Bacterial Survival In Vivo," *Infection and Immunity* 72(7):4010-4022, 2004.
International Search Report (US), dated Aug. 17, 2006, for PCT/US05/023553, 6 pages.
Iversen et al., "Antisense Antiviral Compound and Method for Treating ssRNA Viral Infection," Office Action, dated Oct. 19, 2010, U.S. Appl. No. 11/432,031, 25 pages.
Iversen et al., "Splice-Region Antisense Composition and Method," Office Action, dated Apr. 23, 2010, U.S. Appl. No. 11/433,214, 17 pages.
Jackowski et al., "Ratio of active to inactive forms of acyl carrier protein in *Escherichia coli*," *J. Biol. Chem.* 258(24):15186-15191, 1983.
Jackson et al., "*Escherichia coli* O157:H7 diarrhoea associated with well water and infected cattle on an Ontario farm," *Epidemiol Infect* 120(1):17-20, 1998.
Knudsen et al., "Antisense properties of duplex- and triplex-forming PNAs," *Nucleic Acids Res* 24(3):494-500, 1996.
Lutkenhaus et al., "Bacterial Cell Division and the Z Ring," *Annu. Rev. Biochem.* 66:93-116, 1997.
Mellbye et al., "Variation in Amino Acid Composition of Antisense Peptide-Phosphorodiamidate Morpholimo Oligomer Affect Potency against *Escherichia coli* In Vitro and In Vivo," *Antimicrobial Agents and Chemotherapy* 53(2):525-530, Feb. 2009.

Mitev et al., "Inhibition of Intracellular Growth of *Salmonella enteric* Serovar Typhimurium in Tissue Culture by Antisense Peptide-Phosphorodiamidate Morpholino Oligomer," *Antimicrobial Agents and Chemotherapy* 53(9):3700-3704, 2009.
Nekhotiaeva et al., "Inhibition of *Staphylococcus aureus* Gene Expression and Growth Using Antisense Peptide Nucleic Acids," *Molecular Therapy* 10(4):652-659, 2004.
Nielsen, "Peptide nucleic acids as antibacterial agents via the antisense principle," *Exp. Opin. Invest. Drugs* 10(2):331-341, 2001.
Nielsen, "Peptide nucleic acids: on the road to new gene therapeutic drugs," *Pharmacol. Toxicol.* 86(1):3-7, 2000.
Nielsen et al., "Sequence-selective recognition of DNA by strand displacement with a thymine-substituted polyamide," *Science* 254(5037):1497-1500, 1991.
Nikaido, "Transport across the bacterial outer membrane," *J Bioenerg Biomembr* 25(6):581-589, 1993.
Petersen et al., "Synthesis of thymidine dimers containing piperazine in the internucleoside linkage and their incorporation into oligodeoxynucleotides," *Tetrahedron* 51:2145-2154, 1995.
Polacco et al., "A mutant of *Escherichia coli* conditionally defective in the synthesis of holo-[acyl carrier protein]," *J. Biol. Chem.* 256(11):5750-5754, 1981.
Rahman et al., "Antibacterial Activity and Inhibition of Protein Synthesis in *Escherichia coli* by Antisense DNA Analogs," *Antisense Research and Development* 1(4):319-327, 1991.
Summerton, *Peptide Nucleic Acids, Morpholinos, and Related Antisense Biomolecules*, Landes Bioscience/Eurekah.com and Kluwer Academic/Plenum Publishers, ed. C.G Janson and M.J. During, 2006, Chapter 6, "Morpholinos and PNAs Compared," pp. 89-113.
Tan et al., "Peptide Nucleic Acid Antisense Oligomer as a Therapeutic Strategy against Bacterial Infection: Proof of Principle Using Mouse Intraperitoneal Infection," *Antimicrobial Agents and Chemotherapy* 49(8):3203-3207, Aug. 2005.
Ex Parte Thumm, 132 USPQ 66, 1961, 3 pages.
Tilley et al., "Gene-Specific Effects of Antisense Phosphorodiamidate Morpholino Oligomer-Peptide Conjugates on *Escherichia coli* and *Salmonella enteric* Serovar Typhimurium in Pure Culture and in Tissue Culture," *Antimicrobial Agents and Chemotherapy* 50(8):2789-2796, Aug. 2006.
Tilley et al., "Antisense peptide-phosphorodiamidate morpholino oligomer conjugate: dose-response in mice infected with *Escherichia coli*," *Journal of Antimicrobial Chemotherapy* 59:66-73, 2007.
Wang et al., "Assessment of the utilization of the antisense RNA strategy to Identify essential genes in heterologous bacteria," *FEMS Microbiology Letters* 220(2):171-176, 2003.
Weller et al., "Oligonucleotide Analogs Having Cationic Intersubunit Linkages," Office Action, dated Aug. 18, 2010, U.S. Appl. No. 11/801,885, 6 pages.
Weller et al., "Oligonucleotide Analogs Having Cationic Intersubunit Linkages," Advisory Action, dated Oct. 28, 2010, U.S. Appl. No. 11/801,885, 6 pages.
Wiersinga, "Beyond Antibiotics: New Horizons in Treating Burkholderia Species Infections," *The Journal of Infectious Diseases* 201(12), Jun. 2010, 2 pages.
Youngblood et al., "Stability of Cell-Penetrating Peptide—Morpholino Oligomer Conjugates in Human Serum and in Cells," *Bioconjugate Chem.* 18:50-60, 2007.
Zhang et al., "Polar Allele Duplication for Transcriptional Analysis of Consecutive Essential Genes: Application to a Cluster of *Escherichia coli* Fatty Acid Biosynthetic Genes," *Journal of Bacteriology* 178(12):3614-3620, Jun. 1996.
Zollinger et al., "Meningococcal vaccines—present and future," *Transactions of Royal Soc of Tropical Medicine and Hygiene* 85(Supp. 1):37-43, 1991.
Kang et al., "Stacking Interactions of ApA Analogues with Modified Backbones," *Biopolymers* 32:1351-1363, 1992.

* cited by examiner

BORONIC ACID CONJUGATES OF OLIGONUCLEOTIDE ANALOGUES

STATEMENT REGARDING SEQUENCE LISTING

The Sequence Listing associated with this application is provided in text format in lieu of a paper copy, and is hereby incorporated by reference into the specification. The name of the text file containing the Sequence Listing 120178_497WO_SEQUENCE_LISTING.txt. The text file is 8 KB, was created on Mar. 7, 2013, and is being submitted electronically via EFS-Web.

BACKGROUND

Technical Field

The present invention is generally related to oligonucleotide analogues (oligomers) useful as antisense compounds, and more particularly to boronic acid conjugates of oligonucleotide analogues, and the use of such oligonucleotide analogues in antisense applications.

Description of the Related Art

Antisense oligomers are generally designed to bind to DNA or RNA of disease-causing proteins to prevent the production of such proteins. Requirements for successful implementation of antisense therapeutics include (a) stability in vivo, (b) sufficient membrane permeability and cellular uptake, and (c) a good balance of binding affinity and sequence specificity. Many oligonucleotide analogues have been developed in which the phosphodiester linkages of native DNA are replaced by other linkages that are resistant to nuclease degradation (see, e.g., Barawkar, D. A. et al., *Proc. Na't'l Acad. Sci. USA* 95(19):11047-52 (1998); Linkletter, B. A. et al., *Nucleic Acids Res.* 29(11):2370-6 (2001); Micklefield, J., *Curr, Med, Chem,* 8(10):1157-79 (2001)). Antisense oligonucleotides having other various backbone modifications have also been prepared (Crooke, S. T., *Antisense Drug Technology: Principles, Strategies, and Applications*, New York, Marcel Dekker (2001); Micklefield, J., *Curr, Med, Chem,* 8(10):1157-79 (2001); Crooke, S. T., *Antisense Drug Technology*, Boca Raton, CRC Press (2008)). In addition, oligonucleotides have been modified by peptide conjugation in order to enhance cellular uptake (Moulton, H. M. et al., *Bioconjug Chem* 15(2):290-9 (2004); Nelson, M. H. et al., *Bioconjug. Chem.* 16(4):959-66 (2005); Moulton, H. M. et al., *Biochim Biophys Acta* (2010)).

The performance of such nucleic acid analogues as antisense or antigene drugs has been hampered by certain characteristics of the various analogues. For example, analogues with negatively charged linkages, including phosphorothioate-linked analogues, suffer from considerable electrostatic repulsion between the negative charges of the oligomer and the DNA or RNA target. The phosphorothioates also exhibit non-specific binding to other cellular components such as proteins. These attributes limit the therapeutic effectiveness of antisense oligomers comprised of native RNA, native DNA, and negatively charged analogues (Crooke, S. T., *Antisense Drug Technology: Principles, Strategies, and Applications*, New York, Marcel Dekker (2001); Crooke, S. T., *Antisense Drug Technology*, Boca Raton, CRC Press (2008)). The nonionic methylphosphonate-linked oligonucleotide analogues can be transported into cells by passive diffusion and/or fluid phase endocytosis, but their use is hampered by stereoisomeric complexity and poor solubility (Crooke, S. T., *Antisense Drug Technology: Principles, Strategies, and Applications*, New York, Marcel Dekker (2001); Micklefield, J., *Curr, Med, Chem,* 8(10):1157-79 (2001)).

Several groups have reported the synthesis of positively charged oligonucleotides (Bailey, C. P. et al. *Nucleic Acids Res.* 26(21):4860-7 (1998); Micklefield, J., *Curr, Med, Chem,* 8(10):1157-79 (2001); Egli, M. et al., *Biochemistry* 44(25):9045-57 (2005)). For example, a class of guanidinium linked nucleosides (designated DNG), formed by replacement of the phosphate linkages in DNA and RNA by achiral guanidino groups, has been reported (Dempcy, R. O. et al., *Proc. Nat'l Acad. Sci. USA* 91(17):7864-8 (1994); Dempcy, R. O. et al., *Proc. Nat'l Acad. Sci. USA* 93(9): 4326-30 (1996); Barawkar, D. A. et al., *Proc. Na't'l Acad. Sci. USA* 95(19):11047-52 (1998); Linkletter, B. A. et al., *Nucleic Acids Res.* 29(11):2370-6 (2001)). Oligomers linked with positively charged methylated thiourea linkages have also been reported (Arya, D. P. et al., *Proc. Nat'l Acad. Sci. USA* 96(8): 4384-9 (1999)). Replacement of some of these linkages with neutral urea linkages has been reported to reduce the tendency of such positively charged oligomers towards non-sequence-specific binding (Linkletter, B. A. et al., *Bioorg. Med. Chem.* 8(8):1893-901 (2000)). Morpholino oligomers containing (1-piperazino) phosphinylideneoxy and (1-(4-(w-guanidino-alkanoyl))-piperazino) phosphinylideneoxy linkages have been described previously (see e.g., WO2008036127).

Although significant progress has been made, there remains a need in the art for oligonucleotide analogues with improved antisense or antigene performance. Such improved antisense or antigene performance includes; stronger affinity for DNA and RNA without compromising sequence selectivity; improved pharmacokinetics and tissue distribution; improved cellular delivery and reliable and controllable in vivo distribution.

BRIEF SUMMARY

In general, the present invention provides oligonucleotide analogues which provide improvements over existing antisense molecules in the art. In this regard, the present inventors have found that conjugation of a boronic acid or boronic ester moiety to one or more of the intersubunit linkages and/or the 5' and/or 3' terminus of an oligonucleotide analogue, for example a morpholino oligonucleotide, results in an antisense oligomer having superior properties. For example, in certain embodiments the disclosed oligomers have enhanced cell delivery, potency, and/or tissue distribution compared to other oligonucleotide analogues and/or can be effectively delivered to the target organs. These superior properties give rise to favorable therapeutic indices, reduced clinical dosing, and lower cost of goods.

In one embodiment, the present disclosure provides an oligonucleotide analogue comprising a backbone, a 3'-terminus and a 5'-terminus, the backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligonucleotide analogue can bind in a sequence-specific manner to a target nucleic acid, wherein at least one of the intersubunit linkages, the 3'-terminus or the 5'-terminus comprises a boronic acid or boronic ester moiety covalently bound thereto.

In another embodiment, the present disclosure provides a method of inhibiting production of a protein, the method comprising exposing a nucleic acid encoding the protein to an oligomer of the present disclosure.

In another embodiment, the disclosure is directed to a method of treating a disease in a subject, the method comprising administering a therapeutically effective amount of an oligomer as disclosed herein. Methods of making the oligomers and methods for their use are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

I. Definitions

Figure 1:
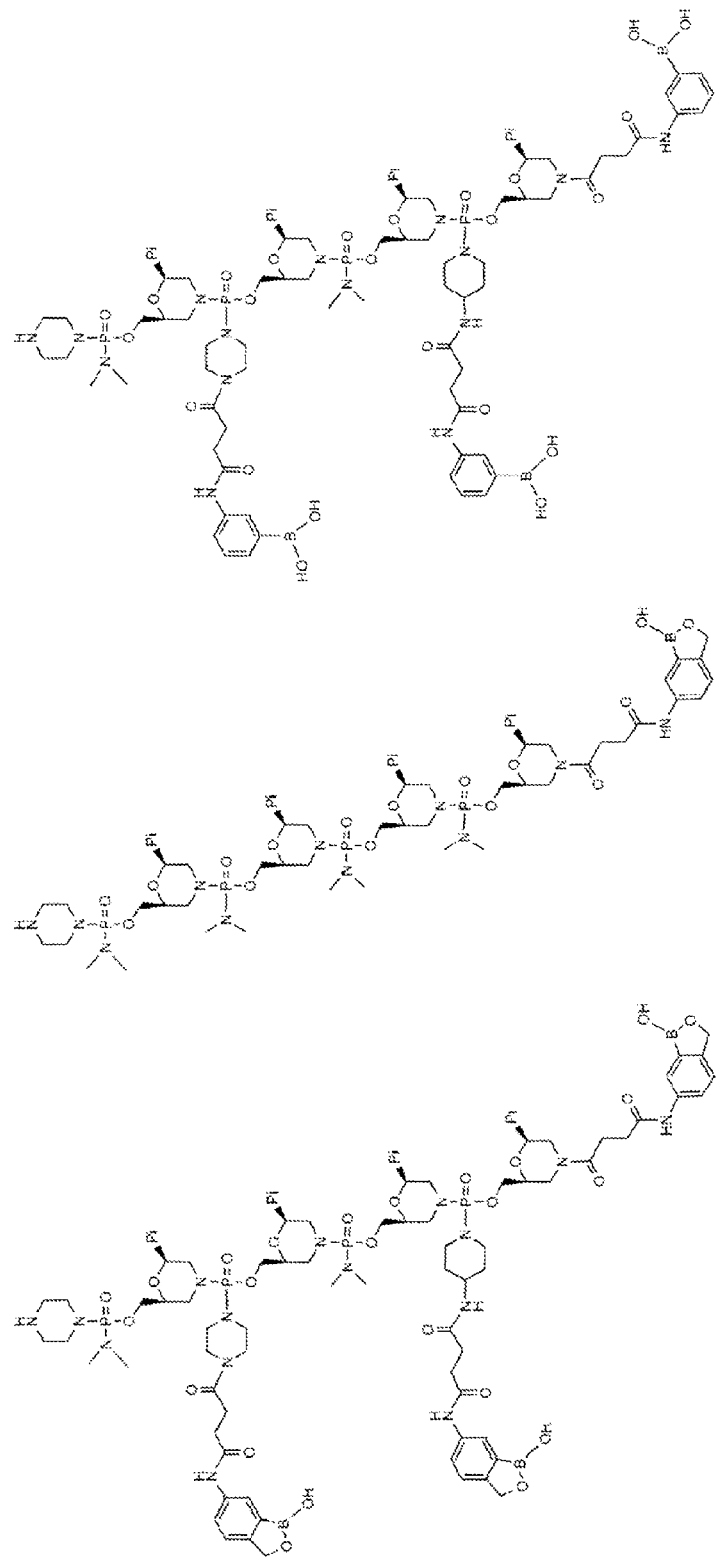
FIG. 1 shows short sequences of exemplary boronic acid-nucleotide conjugates.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —$NH_2$ radical.

"Cyano" or "nitrile" refers to the —CN radical.

"Halo" refers to a fluoro, chloro, bromo or iodo radical.

"Hydroxy" or "hydroxyl" refers to the —OH radical.

"Nitro" refers to the —$NO_2$ radical.

"Oxo" refers to the =O substituent.

A "boronic acid" is a moiety comprising a —$B(OH)_2$ radical.

A "boronic ester) is a moiety comprising a —$(OR_a)_2$ radical, wherein $R_a$ is, at each occurrence, independently H or an alkyl radical as defined below.

"Alkyl" refers to a straight or branched hydrocarbon chain radical which is saturated or unsaturated (i.e., contains one or more double and/or triple bonds), having from one to thirty carbon atoms. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, but-2-ynyl, but-3-ynyl, pentynyl, hexynyl, and the like. Alkyls include saturated, unsaturated and cyclic (cycloalkyl) alkyls. Unless stated otherwise specifically in the specification, an alkyl group may be optionally substituted as described below.

"Alkylene" or "alkylene chain" refers to a straight or branched divalent hydrocarbon chain linking the rest of the molecule to a radical group. Alkylenes may be saturated or unsaturated (i.e., contains one or more double and/or triple bonds). Representative alkylenes include, but are not limited to, $C_1$-$C_{12}$ alkylene, $C_1$-$C_8$ alkylene, $C_1$-$C_6$ alkylene, $C_1$-$C_4$ alkylene, $C_1$-$C_3$ alkylene, $C_1$-$C_2$ alkylene, $C_1$ alkylene. Representative alkylene groups include, but are not limited to, methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted as described below.

"Alkoxy" refers to a radical of the formula —$OR_a$ where $R_a$ is an alkyl radical as defined. Unless stated otherwise specifically in the specification, an alkoxy group may be optionally substituted as described below.

Alkoxyalkyl" refers to a radical of the formula —$R_bOR_a$ where $R_a$ is an alkyl radical as defined and where $R_b$ is an alkylene radical as defined. Unless stated otherwise specifically in the specification, an alkoxyalkyl group may be optionally substituted as described below.

"Alkylcarbonyl" refers to a radical of the formula —C(=O)$R_a$ where $R_a$ is an alkyl radical as defined above. Unless stated otherwise specifically in the specification, an alkylcarbonyl group may be optionally substituted as described below.

"Alkyloxycarbonyl" refers to a radical of the formula —C(=O)$OR_a$ where $R_a$ is an alkyl radical as defined. Unless stated otherwise specifically in the specification, an alkyloxycarbonyl group may be optionally substituted as described below.

"Alkyloxycarbonylaminyl" refers to a radical of the formula —$NR_aC$(=O)$OR_b$ where $R_a$ is hydrogen or an alkyl radical as defined above and $R_b$ is an alkyl radical as defined. Unless stated otherwise specifically in the specification, an alkyloxycarbonyl group may be optionally substituted as described below.

"Alkyloxyimino" refers to a radical of the formula —C(=NH)O—$R_a$, where $R_a$ is an alkyl radical as defined above. Unless stated otherwise specifically in the specification, an alkyloxyimino group may be optionally substituted as described below.

"Alkylamino" refers to a radical of the formula —NHR$_a$ or —NR$_a$R$_a$ where each $R_a$ is, independently, an alkyl radical as defined above. Unless stated otherwise specifically in the specification, an alkylamino group may be optionally substituted as described below.

"Amidyl" refers to a radical of the formula —N($R_a$)C(=O)$R_b$ where $R_a$ is hydrogen or an alkyl or aryl radical and $R_b$ is an alkyl or aryl radical as defined herein. Unless stated otherwise specifically in the specification, an amidyl group may be optionally substituted as described below.

"Aminoalkyl" refers to a radical of the formula —$R_b$—NR$_a$R$_a$ where $R_b$ is an alkylene radical as defined above, and each $R_a$ is independently a hydrogen or an alkyl radical.

"Aminocarbonyl" refers to a radical of the formula —C(=O)NH$_2$.

"Alkylaminocarbonyl" refers to a radical of the formula —C(=O)NR$_a$R$_a$, where each $R_a$ is independently an alkyl radical as defined herein. Unless stated otherwise specifically in the specification, an alkylaminocarbonyl group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl, trityl and the like. Unless stated otherwise specifically in the specification, an aralkyl group may be optionally substituted.

"Arylamino" refers to a radical of the formula —NHR$_a$ or —NR$_a$R$_a$ where each $R_a$ is, independently, an aryl radical as defined above. Unless stated otherwise specifically in the specification, an arylamino group may be optionally substituted as described below.

"Arylaminocarbonyl" refers to a radical of the formula —C(=O)NR$_a$R$_b$, where $R_a$ is an aryl radical as defined herein and $R_b$ is hydrogen or any alkyl radical. Unless stated otherwise specifically in the specification, an arylaminocarbonyl group may be optionally substituted as described below.

"Aralkylamino" refers to a radical of the formula —NR$_b$R$_a$ where each $R_a$ is an aryl radical and $R_b$ is an alkylene chain as defined above. Unless stated otherwise specifically in the specification, an arylamino group may be optionally substituted as described below.

"Aralkylaminocarbonyl" refers to a radical of the formula —C(=O)NR$_b$R$_a$ where each $R_a$ is an aryl radical and $R_b$ is an alkylene chain as defined above. Unless stated otherwise specifically in the specification, an arylamino group may be optionally substituted as described below.

"Arylcarbonyl" refers to a radical of the formula —C(=O)$R_c$, where $R_c$ is one or more aryl radicals as defined above, for example, phenyl. Unless stated otherwise specifically in the specification, an arylcarbonyl group may be optionally substituted.

"Aryloxycarbonyl" refers to a radical of the formula —C(=O)O$R_c$, where $R_c$ is one or more aryl radicals as defined above, for example, phenyl. Unless stated otherwise specifically in the specification, an aryloxycarbonyl group may be optionally substituted.

"Aryloxycarbonylaminyl" refers to a radical of the formula —NR$_a$C(=O)O$R_c$, where $R_a$ is hydrogen or an alkyl radical and $R_c$ is an aryl radical as defined above, for example, phenyl. Unless stated otherwise specifically in the specification, an aryloxycarbonyl group may be optionally substituted.

"Aralkylcarbonyl" refers to a radical of the formula —C(=O)$R_b$—$R_c$ where $R_b$ is an alkylene chain as defined above and $R_c$ is one or more aryl radicals as defined above, for example, phenyl. Unless stated otherwise specifically in the specification, an aralkylcarbonyl group may be optionally substituted.

"Aralkyloxycarbonyl" refers to a radical of the formula —C(=O)O$R_b$—$R_c$, where $R_b$ is an alkylene chain as defined above and $R_c$ is one or more aryl radicals as defined above, for example, phenyl. Unless stated otherwise specifically in the specification, an aralkyloxycarbonyl group may be optionally substituted.

"Aralkyloxycarbonylaminyl" refers to a radical of the formula —NR$_a$C(=O)O$R_b$—$R_c$ where $R_a$ is hydrogen or an alkyl radical, $R_b$ is an alkylene chain as defined above and $R_c$ is one or more aryl radicals as defined above, for example, phenyl. Unless stated otherwise specifically in the specification, an aralkyloxycarbonyl group may be optionally substituted.

"Aryloxy" refers to a radical of the formula —O$R_c$ where $R_c$ is one or more aryl radicals as defined above, for example, phenyl. Unless stated otherwise specifically in the specification, an arylcarbonyl group may be optionally substituted.

"Cycloalkyl" refers to a stable, non-aromatic, monocyclic or polycyclic carbocyclic ring, which may include fused or bridged ring systems, which is saturated or unsaturated, and attached to the rest of the molecule by a single bond. Representative cycloalkyls include, but are not limited to, cycloaklyls having from three to fifteen carbon atoms and from three to eight carbon atoms, Monocyclic cyclcoalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and 7,7-dimethyl-bicyclo[2.2.1]heptanyl. Unless otherwise stated specifically in the specification, a cycloalkyl group may be optionally substituted.

"Carbocyclic" includes cycloalkyls and aryls as defined above.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Heterocyclyl", "heterocycle" or "heterocyclic ring" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4,15-crown-5,18-crown-6,21-crown-7, aza-18-crown-6, diaza-18-crown-6, aza-21-crown-7, and diaza-21-crown-7. Unless stated otherwise specifically in the specification, a heterocyclyl group may be optionally substituted.

"Heteroaryl" is a type of heterocycle and refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"Hydroxyalkyl" refers to a radical of the formula —$R_b$—OH where $R_b$ is an alkylene radical as defined above. Hydroxyalklys include primary, secondary and tertiary alkyl alcohols.

All the above groups may be either substituted or unsubstituted. The term "substituted" as used herein means any of the above groups (i.e., alkyl, alkylene, alkoxy, alkoxyalkyl, alkylcarbonyl, alkyloxycarbonyl, alkyloxycarbonylaminyl, alkyloxyimino, alkylamino, amidyl, aminoalkyl, aminocarbonyl, alkylaminocarbonyl, aryl, aralkyl, arylamino, arylaminocarbonyl, aralkylamino, aralkylaminocarbonyl, arylcarbonyl, aryloxycarbonyl, aralkylcarbonyl, aralkyloxycarbonyl, aralkyloxycarbonylaminyl, aryloxy, cycloalkyl, heterocyclyl, heteroaryl and or hydroxyalkyl), may be further functionalized wherein at least one hydrogen atom is replaced by a bond to a non-hydrogen atom substituent. Unless stated specifically in the specification, a substituted group may include one or more substituents selected from: oxo (=O), —$CO_2H$, nitrile, nitro, —$CONH_2$, hydroxyl, halo, thiooxy (=S), alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$CH_2SO_2R_g$, —$CH_2SO_2NR_gR_h$, —SH, —$SR_g$ or —$SSR_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen or sulfur atoms. For example, an alkyl group may be substituted with one or more internal oxygen atoms to form an ether or polyether group. Similarly, an alkyl group may be substituted with one or more internal sulfur atoms to form a thioether, disulfide, etc.

The terms "antisense oligomer" or "antisense compound" are used interchangeably and refer to a sequence of subunits, each having a base carried on a backbone subunit composed of ribose or other pentose sugar or morpholino group, and where the backbone groups are linked by intersubunit linkages that allow the bases in the compound to hybridize to a target sequence in a nucleic acid (typically an RNA) by Watson-Crick base pairing, to form a nucleic acid:oligomer heteroduplex within the target sequence. The oligomer may have exact sequence complementarity to the target sequence or near complementarity. Such antisense oligomers are designed to block or inhibit translation of the mRNA containing the target sequence, and may be said to be "directed to" a sequence with which it hybridizes.

A "morpholino oligomer" or "PMO" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. An exemplary "morpholino" oligomer comprises morpholino subunit structures linked together by (thio)phosphoramidate or (thio)phosphorodiamidate linkages, joining the morpholino nitrogen of one subunit to the 5' exocyclic carbon of an adjacent subunit, each subunit comprising a purine or pyrimidine base-pairing moiety effective to bind, by base-specific hydrogen bonding, to a base in a polynucleotide. Morpholino oligomers (including antisense oligomers) are detailed, for example, in U.S. Pat. Nos. 5,698,685; 5,217,866; 5,142,047; 5,034,506; 5,166, 315; 5,185,444; 5,521,063; and 5,506,337, US patent application pub. Nos. 2009/0131632; 2009/0131624; and 2012/0065169; and PCT publication number WO/2009/064471 all of which are incorporated herein by reference in their entirety for all purposes. Representative PMOs include PMOs wherein the intersubunit linkages comprise a dimethylamino moiety.

A "phosphoramidate" group comprises phosphorus having three attached oxygen atoms and one attached nitrogen atom, while a "phosphorodiamidate" group (see e.g., FIGS. 1D-E) comprises phosphorus having two attached oxygen atoms and two attached nitrogen atoms. In the uncharged or the modified intersubunit linkages of the oligomers described herein and U.S. Patent Application No. 61/349, 783 and Ser. No. 11/801,885, one nitrogen is always pendant to the backbone chain. The second nitrogen, in a phosphorodiamidate linkage, is typically the ring nitrogen in a morpholino ring structure.

"Intersubunit linkage" refers to the linkage connecting two morpholino subunits, for example structure (I).

An oligonucleotide or antisense oligomer "specifically hybridizes" to a target polynucleotide if the oligomer hybridizes to the target under physiological conditions, with a Tm greater than 37° C., greater than 45° C., preferably at least 50° C., and typically 60° C.-80° C. or higher. The "Tm" of an oligomer is the temperature at which 50% hybridizes to a complementary polynucleotide. Tm is determined under standard conditions in physiological saline, as described, for example, in Miyada et al., *Methods Enzymol.* 154:94-107 (1987). Such hybridization may occur with "near" or "substantial" complementary of the antisense oligomer to the target sequence, as well as with exact complementarity.

Polynucleotides are described as "complementary" to one another when hybridization occurs in an antiparallel configuration between two single-stranded polynucleotides. Complementarity (the degree that one polynucleotide is complementary with another) is quantifiable in terms of the proportion of bases in opposing strands that are expected to form hydrogen bonds with each other, according to generally accepted base-pairing rules.

A first sequence is an "antisense sequence" with respect to a second sequence if a polynucleotide whose sequence is the first sequence specifically binds to, or specifically hybridizes with, the second polynucleotide sequence under physiological conditions.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the presently described methods, that is, still be "complementary." Preferably, the oligonucleotide analog compounds employed in the presently described methods have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein. For purposes of complementary binding to an RNA target, and as discussed below, a guanine base may be complementary to either a cytosineor uracil RNA base.

A "heteroduplex" refers to a duplex between an oligonculeotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAse H, which are capable of cutting double-stranded RNA/RNA or RNA/DNA complexes.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane.

The terms "modulating expression" and/or "antisense activity" refer to the ability of an antisense oligomer to either enhance or, more typically, reduce the expression of a given protein, by interfering with the expression or translation of RNA. In the case of reduced protein expression, the antisense oligomer may directly block expression of a given gene, or contribute to the accelerated breakdown of the RNA transcribed from that gene. Morpholino oligomers as described herein are believed to act via the former (steric blocking) mechanism. Preferred antisense targets for steric blocking oligomers include the ATG start codon region, splice sites, regions closely adjacent to splice sites, and 5'-untranslated region of mRNA, although other regions have been successfully targeted using morpholino oligomers.

An "effective amount" or "therapeutically effective amount" refers to an amount of antisense oligomer administered to a mammalian subject, either as a single dose or as part of a series of doses, which is effective to produce a desired therapeutic effect, typically by inhibiting translation of a selected target nucleic acid sequence.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent.

II. Antisense Oligomers

A. Oligomers Comprising Boronic Acid or Boronic Ester Moieties

As noted above, one embodiment of the present disclosure is directed to oligonucleotide analogues (referred to herein as "oligomers") comprising boronic acid or boronic ester moieties. Boronic acids are known to have special affinity for carbohydrates: they bind in a covalent, bidentate fashion to the 1,2-diol or 1,3-diol unit present in sugars. Boronic acids can thus be considered synthetic lectins. The surface of a eukaryotic or prokaryotic cell contains many carbohydrate structures available for reaction with boronic acids. Compounds of the present invention are antisense phosphorodiamidate oligomers (PMO) containing boronic acids (or boronic esters which are expected to cleave to boronic acids in vivo) that are intended to bind covalently to cell surface carbohydrates, phosphate head groups, and sulfated polysaccharides; once bound, the compounds of the invention undergo uptake and internalization into the interior of the cell, followed by translocation to the cytoplasm and the nucleus where biological action takes place. The presence of a boronic acid(s) moiety is expected to solve a very important, long standing technical problem: cellular delivery. The compounds of the present invention are able to: 1) efficiently penetrate cell membranes and translocate to the cytoplasma and the nucleus; and 2) gain long residence times in plasma, thus avoiding excretion by and accumulation in the kidney. The structural features and properties of the various linkage types and oligomers are described in more detail in the following discussion.

Figure 2:
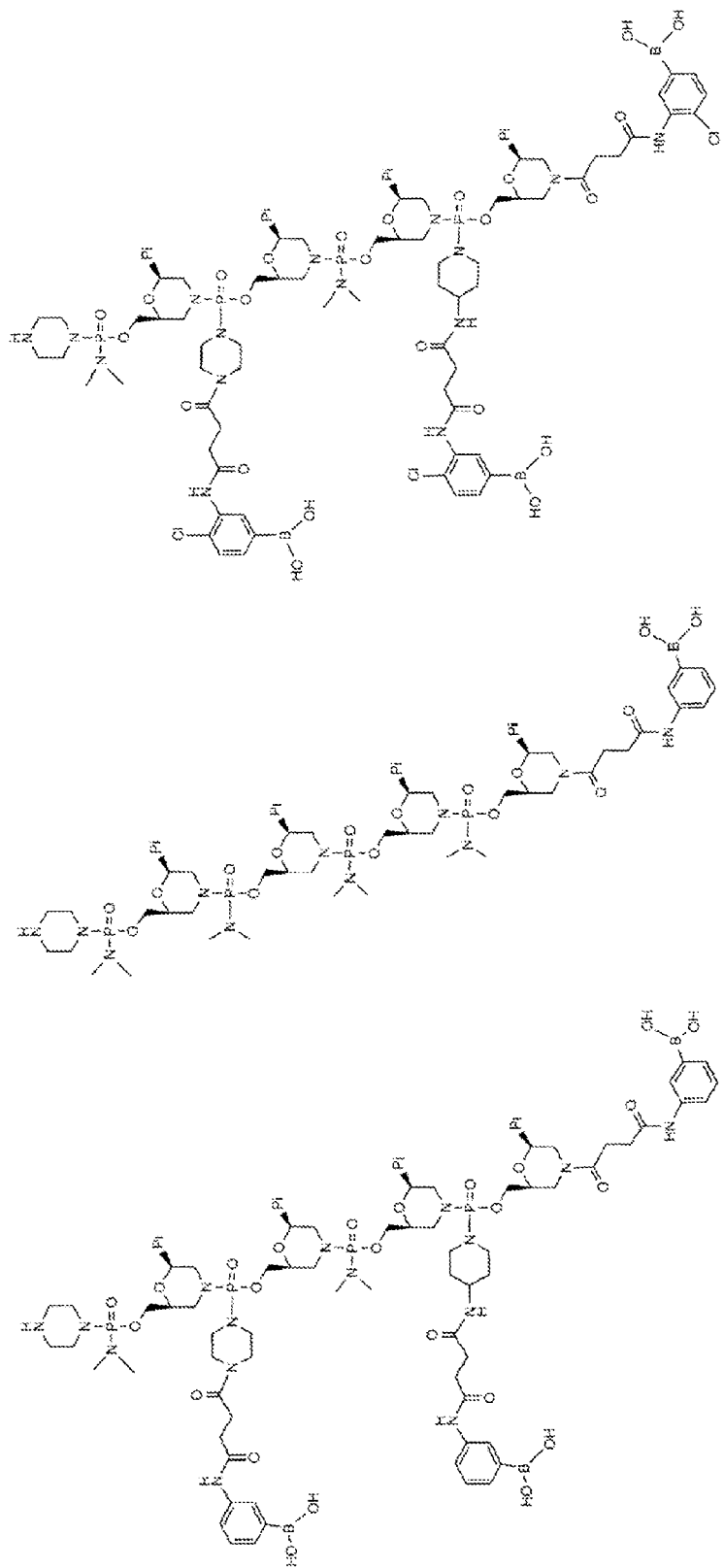
FIG. 2 shows short sequences of exemplary boronic acid-nucleotide conjugates.

FIGS. 1 and 2 provide examples of oligomers of the invention. For purpose of simplicity, the depicted oligomers are shorter than typical. Typically, the oligomers comprise from about 10 to about 30 subunits (i.e., bases). In some embodiments the oligomers comprise from about 18 to about 25 subunits. Further, the examples provided in FIGS. 1 and 2 depict boronic acid conjugates at both the terminal end and at the intersubunit linkages. In actual practice of the invention, the boronic acid (or ester) moiety may be at either the 5'-terminal end, 3'-terminal end or the intersubunit linkage, or any combination thereof. The actual number of boronic acid or boronic ester conjugates in an oligomer is not critical, provided the oligomer comprises at least one of these conjugates. The structural features and properties of the various linkage types and oligomers are described in more detail in the following discussion.

In certain embodiments, the present invention is directed to an oligonucleotide analogue ("oligomer") comprising a backbone, a 3'-terminus and a 5'-terminus, the backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligonucleotide analogue can bind in a sequence-specific manner to a target nucleic acid, wherein at least one of the intersubunit linkages, the 3'-terminus or the 5'-terminus comprises a boronic acid or boronic ester moiety covalently bound thereto.

In some examples, the oligomer comprises at least one linkage comprising a boronic acid or boronic ester moiety covalently bound thereto (a "boron-containing linkage). In some other embodiments, the oligomer includes at least two consecutive born containing linkages. In further embodiments, at least 5% of the linkages in the oligomer are born containing linkages; for example in some embodiments, 5%-95%, 10% to 90%, 10% to 50%, or 10% to 35% of the linkages may be boron containing linkages.

In other embodiments, at least one of the morpholino ring structures has the following structure (i):

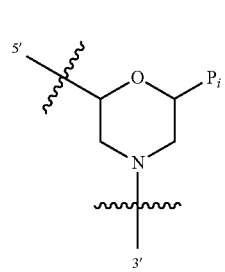

wherein $P_i$ is, at each occurrence, independently a base-pairing moiety.

In still other embodiments of the foregoing oligonucleotide analogue, the boronic acid or boronic ester moiety has, at each occurrence, independently one of the following structures (I) or (II):

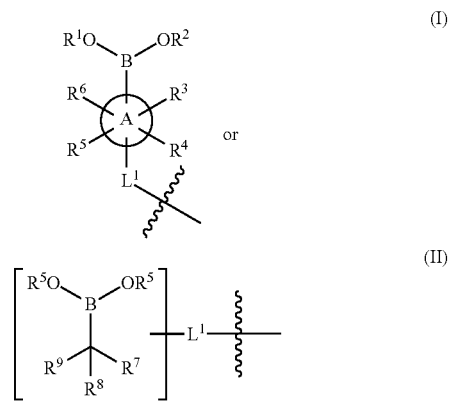

or a pharmaceutically acceptable salt, stereoisomer or tautomer thereof, wherein:

$R^1$ is, at each occurrence, independently H or alkyl;

$R^2$ is H or alkyl, wherein $R^2$ may join with one of $R^3$, $R^4$, $R^5$ or $R^6$ to form a ring;

$R^3$, $R^4$, $R^5$ and $R^6$ are, at each occurrence, independently absent, H, alkyl, hydroxy, hydroxyalkyl, aminoalkyl, alkoxy, aryloxy, halo, nitro, cyano amidyl, amino, alkylamino, arylamino, aralklyamino, aralkyloxycarbonylaminyl, alkyloxycarbonylaminyl, aryloxycarbonylaminyl, —CO$_2$H, alkylcarbonyl, arylcarbonyl, aralkylcarbonyl, aminocarbonyl, alkylaminocarbonyl, arylaminocarbonyl, aralkylaminocarbonyl, alkyloxycarbonyl, alkyloxyimino or heteroaryl, wherein one of $R^3$, $R^4$, $R^5$ or $R^6$ may join with another one of $R^3$, $R^4$, $R^5$ or $R^6$ to form a carbocyclic or heterocyclic ring, and wherein one of $R^3$, $R^4$, $R^5$ or $R^6$ may join with $R^2$ to form a heterocyclic ring;

$R^7$, $R^8$ and $R^9$ are, at each occurrence, independently alkyl or alkyl amino;

A represents, at each occurrence, independently a 6-membered aryl or heteroaryl ring; and $L^1$ is, at each occurrence, independently an optional linker up to 18 atoms in length comprising moieties selected from alkyl, aryl, hydroxyl, alkoxy, ether, amino, heteroaryl, phosphorous, alkylamino, guanidinyl, amidinyl, amide, ester, carbonyl, sulfide, disulfide, carbonyl, carbamate, phosphorodiamidate, phosphoramidate, phosphorothioate, piperazine, phosphodiester and heterocyclyl moieties, wherein

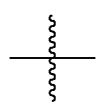

represents a point of covalent attachment of $L^1$ to one of the intersubunit linkages, the 3′-terminus or the 5′-terminus.

In any of the embodiments of the oligonucleotide analogue, the intersubunit linkages have the following structure (III):

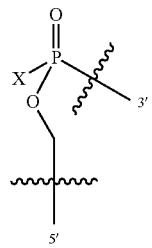

(III)

or a pharmaceutically acceptable salt, stereoisomer or tautomer thereof, wherein:

X is, at each occurrence, independently structure (I), structure (II) or $-NR^{10}R^{11}$; and $R^{10}$ and $R^{11}$ are, at each occurrence, independently hydrogen or $C_1$-$C_6$ alkyl.

In certain embodiments, at least one X is structure (I) or (II). When X is structure (I) or (II), L1 serves as a linkage to covalently attach the P atom in structure (III) to the remainder of structures (I) or (II). In certain other embodiments, at least one X is $-N(CH_3)_2$. In certain more specific embodiments, X is either structure (I) or (II) or $-N(CH_3)_2$, that is each X that is not structure (I) or (II) is $-N(CH_3)_2$. In still other embodiments, the oligonucleotide analogue comprises from 1 to 5 intersubunit linkages which comprise structure (I) or (II), for example in some embodiments X in from 1 to 5 of the intersubunit linkages is structure (I) or (II).

In certain embodiments, the 3′-terminus is covalently linked to structure (I) or structure (II) (via linker $L^1$) and has one of the following structures (IV) or (V):

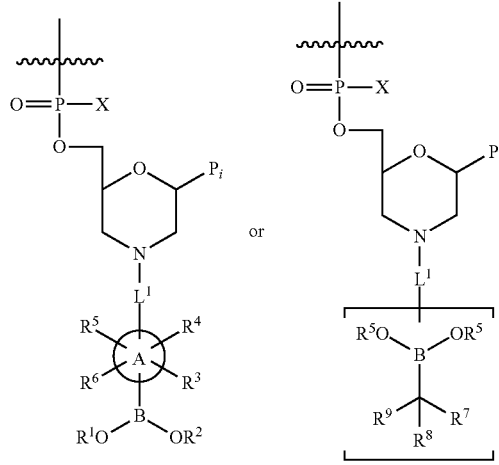

wherein $P_i$ is a base-pairing moiety.

In other embodiments, the 5′-terminus is covalently linked to structure (I) or (II) (via linker $L^1$) and has one of the following structures (VI) or (VII):

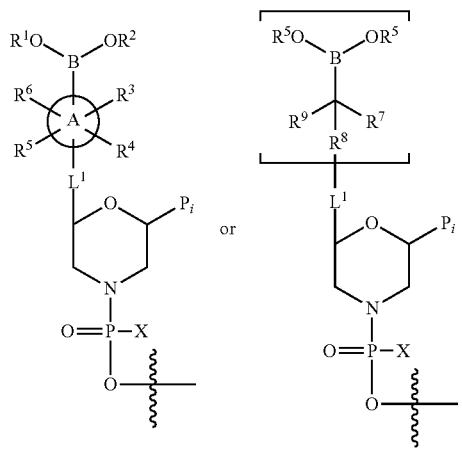

wherein $P_i$ is a base-pairing moiety.

In still other embodiments, structure (I) has one of the following structures (Ia), (Ib), (Ic) or (Id):

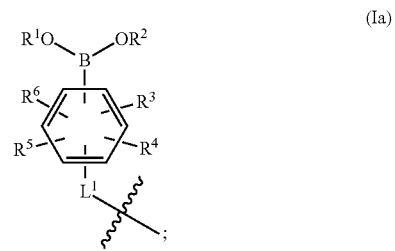

(Ia)

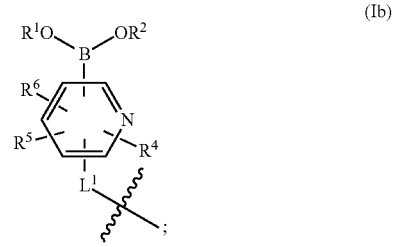

(Ib)

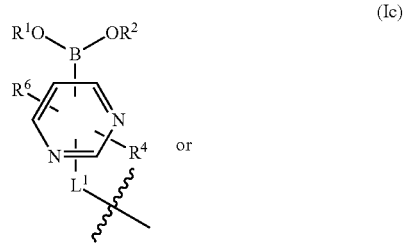

(Ic)

or

-continued

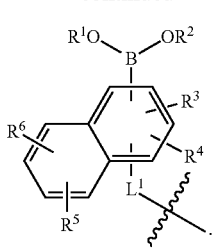
(Id)

Other embodiments include examples wherein structure (II) has one of the following structures (IIa), (IIb), (IIc) or (IId):

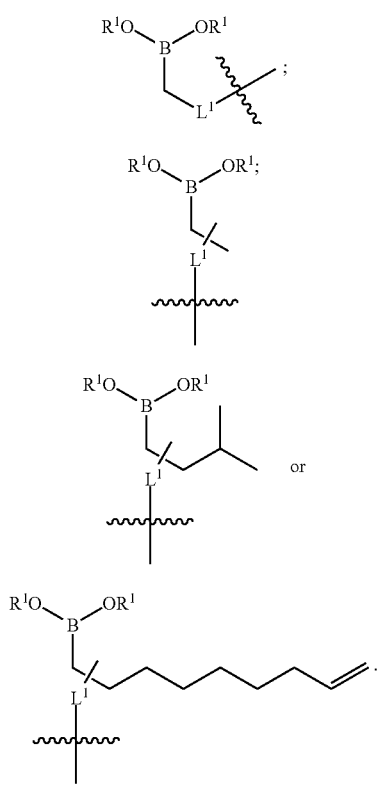

In any of the above embodiments of structure (I), $R^2$ joins with one of $R^3$, $R^4$, $R^5$ or $R^6$ to form a form a heterocyclic ring. For example, in some embodiments, structure (I) has the following structure (Ie):

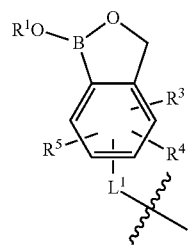
(Ie)

In certain embodiments of any of the preceding embodiments of structures (I) or (II), at least one $R^1$ is H or $R^2$ is H. For example, in some embodiments each $R^1$ and $R^2$ is H.

In still other embodiments of the above, $R^3$, $R^4$, $R^5$ and $R^6$ are each independently absent, H, hydroxyl, alkyl, hydroxyalkyl, aminoalkyl, alkoxy, aryloxy, halo, nitro, cyano amidyl, amino, alkylamino, aryloxycarbonylaminyl, —$CO_2H$, alkyloxycarbonyl, alkyloxyimino or heteroaryl.

In more specific embodiments of the above, structure (I) has a structure selected from any of those depicted in Table 1 below.

TABLE 1

Representative Boron-Containing Moieties

| No. | Structure |
|---|---|
| 1 | 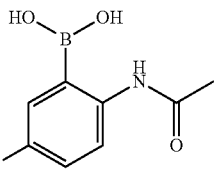 |
| 2 | 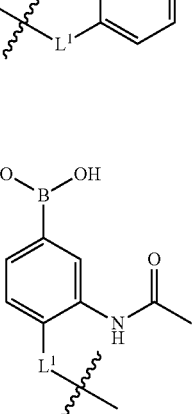 |
| 3 | 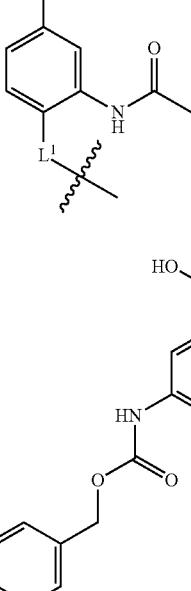 |
| 4 | 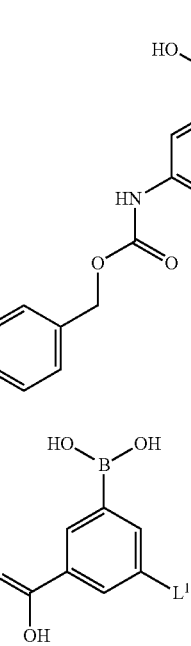 |

TABLE 1-continued

Representative Boron-Containing Moieties

| No. | Structure |
|---|---|
| 5 | (structure) |
| 6 | (structure) |
| 7 | (structure) |
| 8 | (structure) |
| 9 | (structure) |
| 10 | (structure) |
| 11 | (structure) |
| 12 | (structure) |
| 13 | (structure) |
| 14 | (structure) |
| 15 | (structure) |
| 16 | (structure) |
| 17 | (structure) |
| 18 | (structure) |

TABLE 1-continued

Representative Boron-Containing Moieties

| No. | Structure |
|---|---|
| 19 | |
| 20 | |
| 21 | |
| 22 | |
| 23 | |
| 24 | |
| 25 | 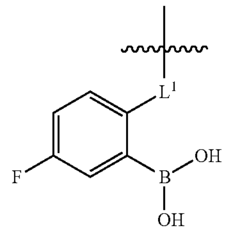 |
| 26 | 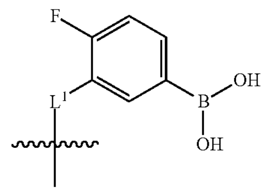 |
| 27 | 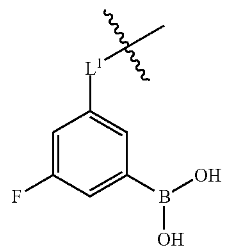 |
| 28 | 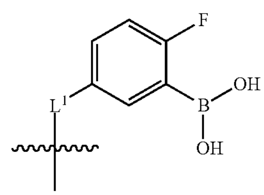 |
| 29 | 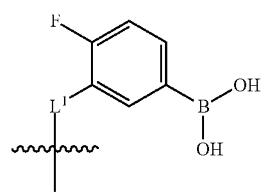 |
| 30 | 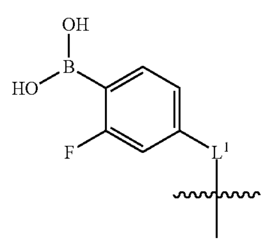 |
| 31 | 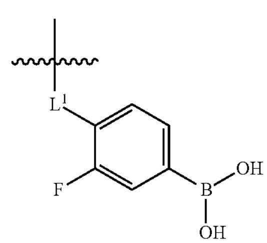 |

TABLE 1-continued

Representative Boron-Containing Moieties

| No. | Structure |
|---|---|
| 32 | (structure) |
| 33 | (structure) |
| 34 | (structure) |
| 35 | (structure) |
| 36 | (structure) |
| 37 | (structure) |
| 38 | (structure) |
| 39 | (structure) |
| 40 | (structure) |
| 41 | (structure) |
| 42 | (structure) |
| 43 | (structure) |
| 44 | (structure) |

TABLE 1-continued

Representative Boron-Containing Moieties

| No. | Structure |
|-----|-----------|
| 45 | 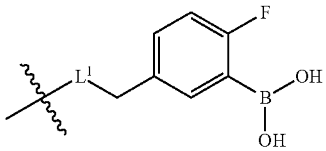 |
| 46 | 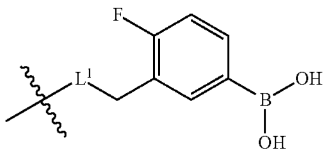 |
| 47 | 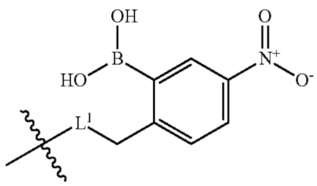 |
| 48 | 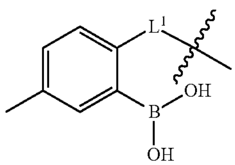 |
| 49 | 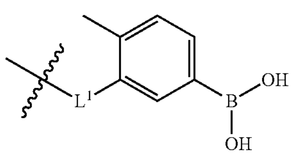 |
| 50 | 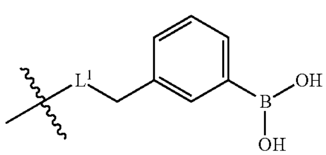 |
| 51 | 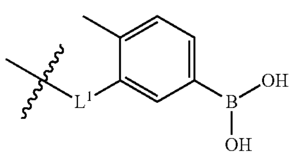 |
| 52 | 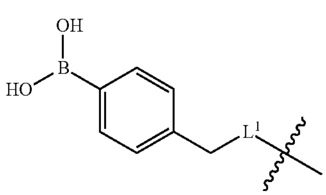 |
| 53 | 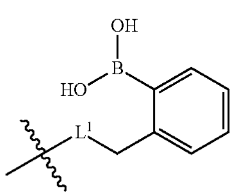 |
| 54 | |
| 55 | |
| 56 | |
| 57 | |
| 58 | |
| 59 | |
| 60 | |
| 61 | |

TABLE 1-continued

Representative Boron-Containing Moieties

| No. | Structure |
|---|---|
| 62 | (structure) |
| 63 | (structure) |
| 64 | (structure) |
| 65 | (structure) |
| 66 | (structure) |
| 67 | (structure) |
| 68 | (structure) |
| 69 | (structure) |
| 70 | (structure) |
| 71 | (structure) |
| 72 | (structure) |
| 73 | (structure) |

As noted above, the linker $L^1$ is optional and serves as a point of covalent attachment between the remainder of structure (I) or (II) and an intersubunit linkage, the 3'-terminal end or the 5'-terminal of the oligonucleotide analogue. The actual structure and length of the linker is not critical so long as it provides a covalent point of attachment and does not interfere with binding of the oligonucleotide analogue to its target sequence. The amide bond provides a facile method for covalent attachment of (I) or (II) to the oligonucleotide analogue, and in some embodiments, $L^1$ comprises amide bonds. In other more specific embodiments, $L^1$ has one of the following structures:

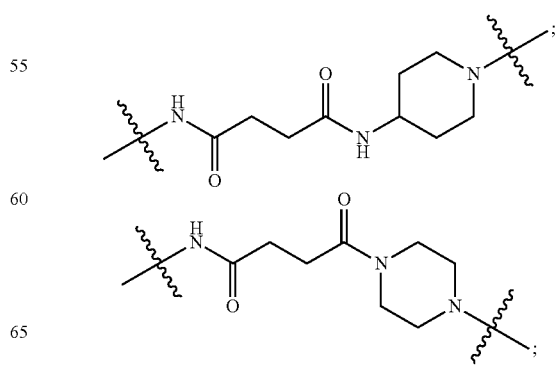

-continued

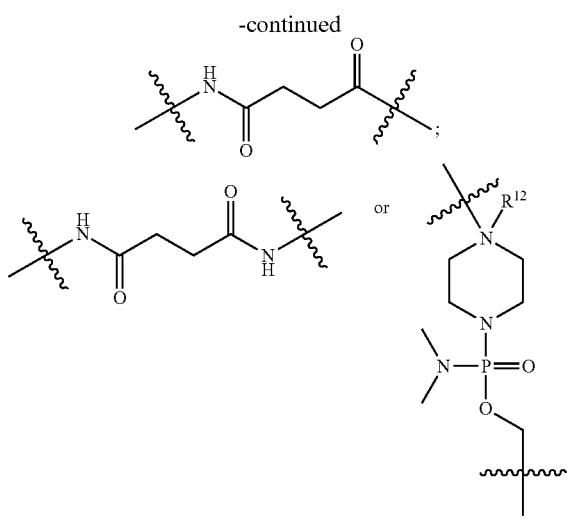

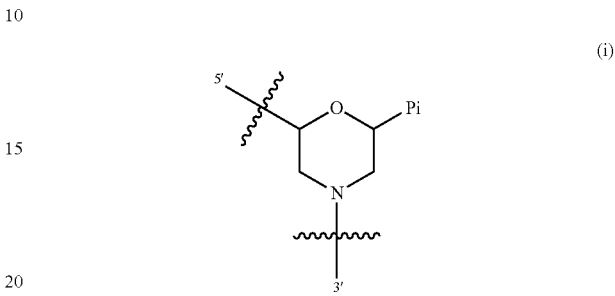

wherein $R^{12}$ is absent, H or $C_1$-$C_6$ alkyl.

In some embodiments of the above oligomers, the 3' or 5'-terminal end may be modified to contain a moiety to improve solubility. Such moieties include triethylene glycol, which may be linked to the oligonucleotide via an L1 linker. Accordingly, some embodiments include oligonucleotide analogues having the following moiety covalently attached at the 3' or 5'-terminal end.

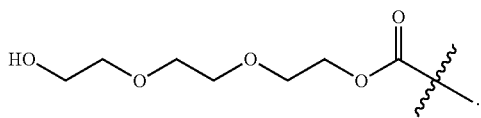 [SMILES: *C(=O)OCCOCCOCCO]

In specific embodiments, the above triethylene glycol moiety is covalently attached at the 5'-terminal end via the following $L^1$ linker:

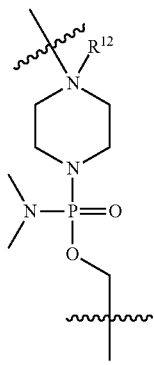

Compositions comprising the oligonucleotide analogue of any one of the above embodiments and a pharmaceutically acceptable vehicle are also contemplated. Pharmaceutical compositions are described in more detail below.

B. Properties of the Oligomers

As noted above, the present disclosure is directed to oligomer comprising boronic acid or boronic ester moieties which impart desirable properties (e.g., better cell penetration, residence time, etc.) to the oligomers. In certain embodiments, the oligomer comprises a backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligomer can bind in a sequence-specific manner to a target nucleic acid. The morpholino ring structures may have the following structure (i):

(i)

wherein Pi is, at each occurrence, independently a base-pairing moiety.

Each morpholino ring structure supports a base pairing moiety (Pi), to form a sequence of base pairing moieties which is typically designed to hybridize to a selected antisense target in a cell or in a subject being treated. The base pairing moiety may be a purine or pyrimidine found in native DNA or RNA (A, G, C, T, or U) or an analog, such as hypoxanthine (the base component of the nucleoside inosine) or 5-methyl cytosine. Analog bases that confer improved binding affinity to the oligomer can also be utilized. Exemplary analogs in this regard include C5-propynyl-modified pyrimidines, 9-(aminoethoxy)phenoxazine (G-clamp) and the like.

As noted above, the oligomer may be modified, in accordance with an aspect of the invention, to include one or more linkages comprising structure (I) or (II), e.g. up to about 1 per every 2-5 linkages, typically 3-5 per every 10 linkages. Certain embodiments also include one or more linkages comprising structure (I) or (II).

In one embodiment, the linkages comprising structure (I) or (II) are interspersed along the backbone. In some embodiments, the oligomer does not have a strictly alternating pattern of linkages comprising structure (I) or (II) linkages along its entire length. The oligomers may optionally comprise a structure (I) or (II) covalently linked to the 5' and/or 3' end.

Oligomers for use in antisense applications generally range in length from about 10 to about 40 subunits, more preferably about 15 to 25 subunits. For example, an oligomer of the invention having 19-20 subunits, a useful length for an antisense oligomer, may ideally have two to seven, e.g. four to six, or three to five, linkages comprising structure (I) or (II). An oligomer having 14-15 subunits may ideally have two to five, e.g. 3 or 4, linkages comprising structure (I) or (II).

In some embodiments for antisense applications, the oligomer may be 100% complementary to the nucleic acid target sequence, or it may include mismatches, e.g., to accommodate variants, as long as a heteroduplex formed between the oligomer and nucleic acid target sequence is sufficiently stable to withstand the action of cellular nucleases and other modes of degradation which may occur in vivo. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the nucleic acid target sequence, it is effective to stably and specifically bind to the target sequence, such that a biological activity of the nucleic acid target, e.g., expression of encoded protein(s), is modulated.

The stability of the duplex formed between an oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, *Methods Enzymol. Vol.* 154 pp. 94-107.

In some embodiments, each antisense oligomer has a binding $T_m$, with respect to a complementary-sequence RNA, of greater than body temperature or in other embodiments greater than 50° C. In other embodiments $T_m$'s are in the range 60-80° C. or greater. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 20 bases or less are generally preferred over those requiring greater than 20 bases for high $T_m$ values. For some applications, longer oligomers, for example longer than 20 bases may have certain advantages. For example, in certain embodiments longer oligomers may find particular utility for use in exon skipping or splice modulation.

The targeting sequence bases may be normal DNA bases or analogues thereof, e.g., uracil and inosine that are capable of Watson-Crick base pairing to target-sequence RNA bases.

The oligomers may also incorporate guanine bases in place of adenine when the target nucleotide is a uracil residue. This is useful when the target sequence varies across different viral species and the variation at any given nucleotide residue is either cytosine or uracil. By utilizing guanine in the targeting oligomer at the position of variability, the well-known ability of guanine to base pair with uracil (termed C/U:G base pairing) can be exploited. By incorporating guanine at these locations, a single oligomer can effectively target a wider range of RNA target variability.

The oligomers may exist in different isomeric forms, for example structural isomers (e.g., tautomers). With regard to stereoisomers, the compounds may have chiral centers and may occur as racemates, enantiomerically enriched mixtures, individual enantiomers, mixture or diastereomers or individual diastereomers. All such isomeric forms are included within the present invention, including mixtures thereof. The compounds may also possess axial chirality which may result in atropisomers. Furthermore, some of the crystalline forms of the compounds may exist as polymorphs, which are included in the present invention. In addition, some of the compounds may also form solvates with water or other organic solvents. Such solvates are similarly included within the scope of this invention.

The oligomers described herein may be used in methods of inhibiting production of a protein or replication of a virus. Accordingly, in one embodiment a nucleic acid encoding such a protein is exposed to an oligomer as disclosed herein. In further embodiments of the foregoing, the antisense oligomer comprises base pairing moieties B which form a sequence effective to hybridize to a portion of a target nucleic acid at a location effective to inhibit production of the protein. In one embodiment, the location is an ATG start codon region of an mRNA, a splice site of a pre-mRNA, or a viral target sequence as described below.

In one embodiment, the oligomer has a $T_m$ with respect to binding to the target sequence of greater than about 50° C., and it is taken up by mammalian cells or bacterial cells. The preparation and properties of morpholino oligomers is described in more detail below and in U.S. Pat. No. 5,185, 444 and WO/2009/064471, each of which is hereby incorporated by reference in their entirety.

C. Formulation and Administration of the Oligomers

The present disclosure also provides for formulation and delivery of the disclosed oligomer. Accordingly, in one embodiment the present disclosure is directed to a composition comprising an oligomer as disclosed herein and a pharmaceutically acceptable vehicle.

Effective delivery of the antisense oligomer to the target nucleic acid is an important aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of a antisense oligomer for the treatment of a viral respiratory infection is by inhalation. The oligomer may also be delivered directly to the site of viral infection, or to the bloodstream.

The antisense oligomer may be administered in any convenient vehicle which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

The compounds (e.g., oligomers) of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate (and esters in general, e.g., boronic esters), formate and benzoate derivatives of alcohol and amine functional groups of the compounds of structure (I). Further, in the case of a carboxylic acid (—COOH), esters may be employed, such as methyl esters, ethyl esters, and the like.

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In one embodiment, antisense inhibition is effective in treating infection of a host animal by a virus, by contacting a cell infected with the virus with an antisense agent effective to inhibit the replication of the specific virus. The antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

In one aspect of the method, the subject is a human subject, e.g., a patient diagnosed as having a localized or systemic viral infection. The condition of a patient may also dictate prophylactic administration of an antisense oligomer of the invention, e.g. in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

In another application of the method, the subject is a livestock animal, e.g., a chicken, turkey, pig, cow or goat, etc, and the treatment is either prophylactic or therapeutic. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

In one embodiment, the antisense compound is administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of disease and/or infection, such as complete blood count (CBC), nucleic acid detection methods, immunodiagnostic tests, viral culture, or detection of heteroduplex.

The efficacy of an in vivo administered antiviral antisense oligomer of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al., Antimicrob. Agents and Chemotherapy 39(5):1157-1161, 1995; Anderson, K. P. et al., Antimicrob. Agents and Chemotherapy 40(9):2004-2011, 1996, Cottral, G. E. (ed) in: Manual of Standard Methods for Veterinary Microbiology, pp. 60-93, 1978).

In some embodiments, the oligomer is actively taken up by mammalian cells. In further embodiments, the oligomer may be conjugated to a transport moiety (e.g., transport peptide) as described herein to facilitate such uptake.

D. Preparation of the Oligomers

The morpholino subunits, the modified intersubunit linkages and oligomers comprising the same can be prepared as described in the examples and in U.S. Pat. Nos. 5,185,444 and 7,943,762 which are hereby incorporated by reference in their entirety. The morpholino subunits can be prepared according to the following general Reaction Scheme I.

Reaction Scheme 1. Preparation of Morpholino Subunits

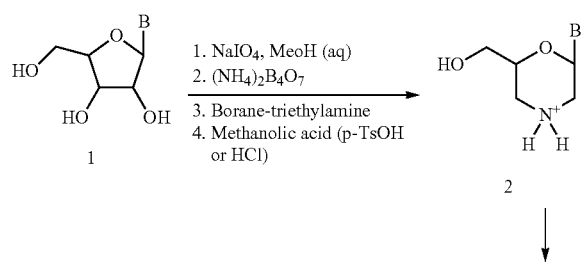

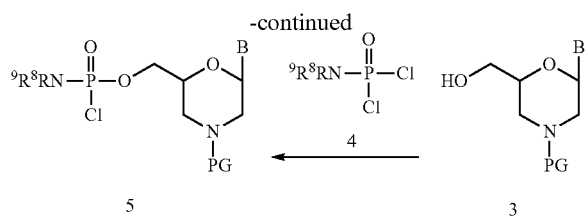

-continued

5  ←4  3

Referring to Reaction Scheme 1, wherein B represents a base pairing moiety and PG represents a protecting group, the morpholino subunits may be prepared from the corresponding ribinucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing poiety may be suitable protected for sold phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in co-pending U.S. application Ser. No. 12/271,040, which is hereby incorporated by reference in its entirety.

Reaction of 3 with the activated phosphorous compound 4, results in morpholino subunits having the desired linkage moiety (5). Compounds of structure 4 can be prepared using any number of methods known to those of skill in the art. For example, such compounds may be prepared by reaction of the corresponding amine and phosphorous oxychloride. In this regard, the amine starting material can be prepared using any method known in the art, for example those methods described in the Examples and in U.S. Pat. No. 7,943,762. Although the above scheme depicts preparation of linkages of type (B) (e.g., X is —$NR^8R^9$), linkages of type (A) (e.g., X is dimethyl amine) can be prepared in an analogous manner.

Compounds of structure 5 can be used in solid-phase automated oligomer synthesis for preparation of oligomers comprising the intersubunit linkages. Such methods are well known in the art. Briefly, a compound of structure 5 may be modified at the 5' end to contain a linker to a solid support. For example, compound 5 may be linked to a solid support by a linker comprising $L^1$. An exemplary method is demonstrated in FIGS. 3 and 4. In this manner, the oligo may comprise a 5'-terminal modification after oligomer synthesis is complete and the oligomer is cleaved from the solid support. Once supported, the protecting group of 5 (e.g., trityl) is removed and the free amine is reacted with an activated phosphorous moiety of a second compound of structure 5. This sequence is repeated until the desired length oligo is obtained. The protecting group in the termina 5' end may either be removed or left on if a 5'-modification is desired. The oligo can be removed from the solid support using any number of methods, or example treatment with a base to cleave the linkage to the solid support.

The preparation of morpholino oligomers containing boronic acid or boronic acide ester moieties are described in more detail in the Examples. In general, the boronic acid (or ester) moiety is prepared according to methods known in the art. A suitable linkage, for example a carboxylic acid-containing moiety, is covalently attached to the boronic acid moiety. Conjugation of the boronic acid moiety is then completed by activation of the boronic acid with a suitable activating agent (e.g., EDC and the like) in the presence of an oligomer containing a free amine.

E. Methods of Treating Diseases with the Oligomers

In other embodiments, the present invention is directed to a method of treating a disease in a mammalian subject, the method comprising administering a therapeutically effective amount of an oligonucleotide analogue of any of the preceding claims to a subject in need thereof.

The present disclosure also provides a method of inhibiting production of a protein, the method comprising exposing a nucleic acid encoding the protein to an oligomer as disclosed herein. Accordingly, in one embodiment a nucleic acid encoding such a protein is exposed to an antisense oligomer comprising at least one boronic acid or boronic acide ester moiety, as disclosed herein, where the base pairing moieties Pi form a sequence effective to hybridize to a portion of the nucleic acid at a location effective to inhibit production of the protein. The oligomer may target, for example, an ATG start codon region of an mRNA, a splice site of a pre-mRNA, or a viral target sequence as described below.

In another embodiment, the disclosure provides a method of enhancing antisense activity of an oligomer having a sequence of morpholino subunits, joined by intersubunit linkages, supporting base-pairing moieties, the method comprises modifying an oligomer as described herein to at least one boronic acid or boronic ester moiety.

In some embodiments, enhancement of antisense activity may be evidenced by:

(i) a decrease in expression of an encoded protein, relative to that provided by a corresponding unmodified oligomer, when binding of the antisense oligomer to its target sequence is effective to block a translation start codon for the encoded protein, or (ii) an increase in expression of an encoded protein, relative to that provided by a corresponding unmodified oligomer, when binding of the antisense oligomer to its target sequence is effective to block an aberrant splice site in a pre-mRNA which encodes said protein when correctly spliced. Assays suitable for measurement of these effects are described further below. In one embodiment, modification provides this activity in a cell-free translation assay, a splice correction translation assay in cell culture, or a splice correction gain of function animal model system as described herein. In one embodiment, activity is enhanced by a factor of at least two, at least five or at least ten.

Described below are various exemplary applications of the oligomers of the invention. This description is not meant to limit the invention in any way but serves to exemplify the range of human and animal disease conditions that can be addressed using oligomers comprising the modified intersubunit linkages described herein.

1. Neuromuscular Diseases

In certain embodiments, the disease is a neuromuscular disease, for example Duchenne muscular dystrophy. In some embodiments, the oligonucleotide analogue for treating neuromuscular disease may be selected from the group consisting of:

(a) an antisense oligomer targeted against human myostatin, having a base sequence complementary to at least 12 contiguous bases in a target region of the human myostatin mRNA identified by SEQ ID NO: 1, for treating a muscle wasting condition, as described previously (See, e.g., U.S. patent application Ser. No. 12/493,140, which is incorporated herein by reference; and PCT publication WO2006/086667). Exemplary murine targeting sequences are listed as SEQ ID NOs: 2-4.

(b) an antisense oligomer capable of producing exon skipping in the DMD protein (dystrophin), such as a PMO having a sequence selected from SEQ ID NOs: 5-18 and 39, to restore partial activity of the dystrophin protein, for treating DMD, as described previously (See, e.g., PCT Pubn. Nos. WO/2010/048586 and WO/2006/000057 or U.S. Patent Publication U.S. Ser. No. 09/061,960 all of which are incorporated herein by reference).

Several other neuromuscular diseases can be treated using the oligomers of the present invention. Exemplary compounds for treating spinal muscle atrophy (SMA) and myotonic dystrophy (DM) are discussed below. SMA is an autosomal recessive disease caused by chronic loss of alpha-motor neurons in the spinal cord and can affect both children and adults. Reduced expression of survival motor neuron (SMN) is responsible for the disease (Hua, Sahashi et al. 2010). Mutations that cause SMA are located in the SMN1 gene but a paralogous gene, SMN2, can allow viability by compensating for loss of SMN1 if expressed from an alternative splice form lacking exon 7 (delta7 SMN2). Antisense compounds targeted to intron 6, exon 7 and intron 7 have all been shown to induce exon 7 inclusion to varying degrees. Antisense compounds targeted to intron 7 are employed in certain embodiments (see e.g., PCT Publication Nos. WO/2010/148249, WO/2010/120820, WO/2007/002390 and U.S. Pat. No. 7,838,657). Exemplary antisense sequences that target the SMN2 pre-mRNA and induce improved exon 7 inclusion are listed below as SEQ ID NOs: 19-21. It is contemplated that selected modifications of these oligomer sequences using the boronic acid or boronic ester moieties described herein would have improved properties compared to those known in the art. Furthermore, it is contemplated that any oligomer targeted to intron 7 of the SMN2 gene and incorporating the features of the present invention has the potential to induce exon 7 inclusion and provide a therapeutic benefit to SMA patients. Myotonic Dystrophy type 1 (DM1) and type 2 (DM2) are dominantly inherited disorders caused by expression of a toxic RNA leading to neuromuscular degeneration. DM1 and DM2 are associated with long polyCUG and polyCCUG repeats in the 3'-UTR and intron 1 regions of the transcript dystrophia myotonica protein kinase (DMPK) and zinc finger protein 9 (ZNF9), respectively (see e.g., WO2008/036406). While normal individuals have as many as 30 CTG repeats, DM1 patients carry a larger number of repeats ranging from 50 to thousands. The severity of the disease and the age of onset correlates with the number of repeats. Patients with adult onsets show milder symptoms and have less than 100 repeats, juvenile onset DM1 patients carry as many as 500 repeats and congenital cases usually have around a thousand CTG repeats. The expanded transcripts containing CUG repeats form a secondary structure, accumulate in the nucleus in the form of nuclear foci and sequester RNA-binding proteins (RNA-BP). Several RNA-BP have been implicated in the disease, including muscleblind-like (MBNL) proteins and CUG-binding protein (CUGBP). MBNL proteins are homologous to *Drosophila* muscleblind (Mbl) proteins necessary for photoreceptor and muscle differentiation. MBNL and CUGBP have been identified as antagonistic splicing regulators of transcripts affected in DM1 such as cardiac troponin T (cTNT), insulin receptor (IR) and muscle-specific chloride channel (ClC-1).

It is known in the art that antisense oligonucleotides targeted to the expanded repeats of the DMPK gene can displace RNA-BP sequestration and reverse myotonia symptoms in an animal model of DM1 (WO2008/036406). It is contemplated that oligomers incorporating features of the present invention would provide improved activity and therapeutic potential for DM1 and DM2 patients. Exemplary sequences targeted to the polyCUG and polyCCUG repeats described above are listed below as SEQ ID NOs: 22-38 and further described in U.S. application Ser. No. 13/101,942 which is incorporated herein in its entirety.

Additional embodiments of the present invention for treating neuralmuscular disorders are anticipated and include oligomers designed to treat other DNA repeat instability genetic disorders. These diseases include Huntington's disease, spino-cerebellar ataxia, X-linked spinal and bulbar muscular atrophy and spinocerebellar ataxia type 10 (SCA10) as described in WO2008/018795.

TABLE 2

Exemplary Oligonucleotide Sequences

| Name | Sequence (5' to 3') | SEQ ID NO |
|---|---|---|
| huMSTN target | GAAAAAAGATTATATTGATTTTAAAATCATGCAAAAACTGCAACTCTGTGTT | 1 |
| muMSTN25-104 | CATACATTTGCAGTTTTTGCATCAT | 2 |
| muMSTN25-183 | TCATTTTTAAAAATCAGCACAATCTT | 3 |
| muMSTN25-194 | CAGTTTTTGCATCATTTTTAAAAATC | 4 |
| Exon44-A | GATCTGTCAAATCGCCTGCAGGTAA | 5 |
| Exon44-B | AAACTGTTCAGCTTCTGTTAGCCAC | 6 |
| Exon44-C | TTGTGTCTTTCTGAGAAACTGTTCA | 7 |
| Exon45-A | CTGACAACAGTTTGCCGCTGCCCAA | 8 |
| Exon45-B | CCAATGCCATCCTGGAGTTCCTGTAA | 9 |
| Exon45-C | CATTCAATGTTCTGACAACAGTTTGCCGCT | 10 |
| Exon50-A | CTTACAGGCTCCAATAGTGGTCAGT | 11 |
| Exon50-B | CCACTCAGAGCTCAGATCTTCTAACTTCC | 12 |
| Exon50-C | GGGATCCAGTATACTTACAGGCTCC | 13 |
| Exon51-A | ACATCAAGGAAGATGGCATTTCTAGTTTGG | 14 |
| Exon51-B | CTCCAACATCAAGGAAGATGGCATTTCTAG | 15 |
| Exon51-C | GAGCAGGTACCTCCAACATCAAGGAA | 16 |
| Exon53-A | CTGAAGGTGTTCTTGTACTTCATCC | 17 |
| Exon53-B | TGTTCTTGTACTTCATCCCACTGATTCTGA | 18 |
| SMN2-A | CTTTCATAATGCTGGCAG | 19 |
| SMN2-B | CATAATGCTGGCAG | 20 |
| SMN2-C | GCTGGCAG | 21 |
| CAG 9mer | CAG CAG CAG | 22 |
| CAG 12mer | CAG CAG CAG CAG | 23 |
| CAG 15mer | CAG CAG CAG CAG CAG | 24 |
| CAG 18mer | CAG CAG CAG CAG CAG CAG | 25 |
| AGC 9mer | AGC AGC AGC | 26 |
| AGC 12mer | AGC AGC AGC AGC | 27 |
| AGC 15mer | AGC AGC AGC AGC AGC | 28 |
| AGC 18mer | AGC AGC AGC AGC AGC AGC | 29 |
| GCA 9mer | GCA GCA GCA | 30 |
| GCA 12mer | GCA GCA GCA GCA | 31 |
| GCA 15mer | GCA GCA GCA GCA GCA | 32 |
| GCA 18mer | GCA GCA GCA GCA GCA GCA | 33 |

TABLE 2-continued

Exemplary Oligonucleotide Sequences

| Name | Sequence (5' to 3') | SEQ ID NO |
|---|---|---|
| AGC 25mer | AGC AGC AGC AGC AGC AGC AGC AGC A | 34 |
| CAG 25mer | CAG CAG CAG CAG CAG CAG CAG CAG C | 35 |
| CAGG 9mer | CAG GCA GGC | 36 |
| CAGG 12mer | CAG GCA GGC AGG | 37 |
| CAGG 24mer | CAG GCA GGC AGG CAG GCA GGC AGG | 38 |
| M23D | GGCCAAACCTCGGCTTACCTGAAAT | 39 |

EXAMPLES

Unless otherwise noted, all chemicals were obtained from Sigma-Aldrich-Fluka. Benzoyl adenosine, benzoyl cytidine, and phenylacetyl guanosine were obtained from Carbosynth Limited, UK.

Synthesis of PMO and PMO containing further linkage modifications as described herein was done using methods known in the art and described in U.S. Pat. Nos. 5,698,685; 5,217,866; 5,142,047; 5,034,506; 5,166,315; 5,185,444; 5,521,063; and 5,506,337, US patent application pub. Nos. 2009/0131632; 2009/0131624; and 2012/0065169; and PCT publication number WO/2009/064471, which have previously been incorporated by reference in their entirety for all purposes.

Example 1

Conjugation of Boronic Acid to 5'-Terminal End

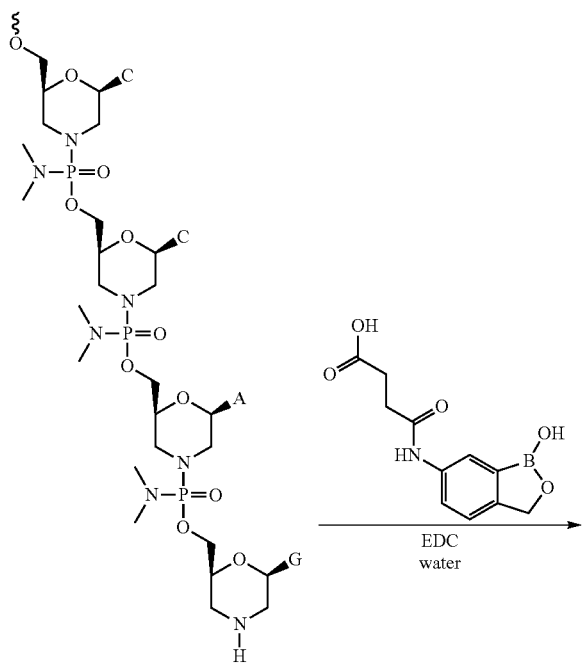

Compound 1 (EGFP sequence)

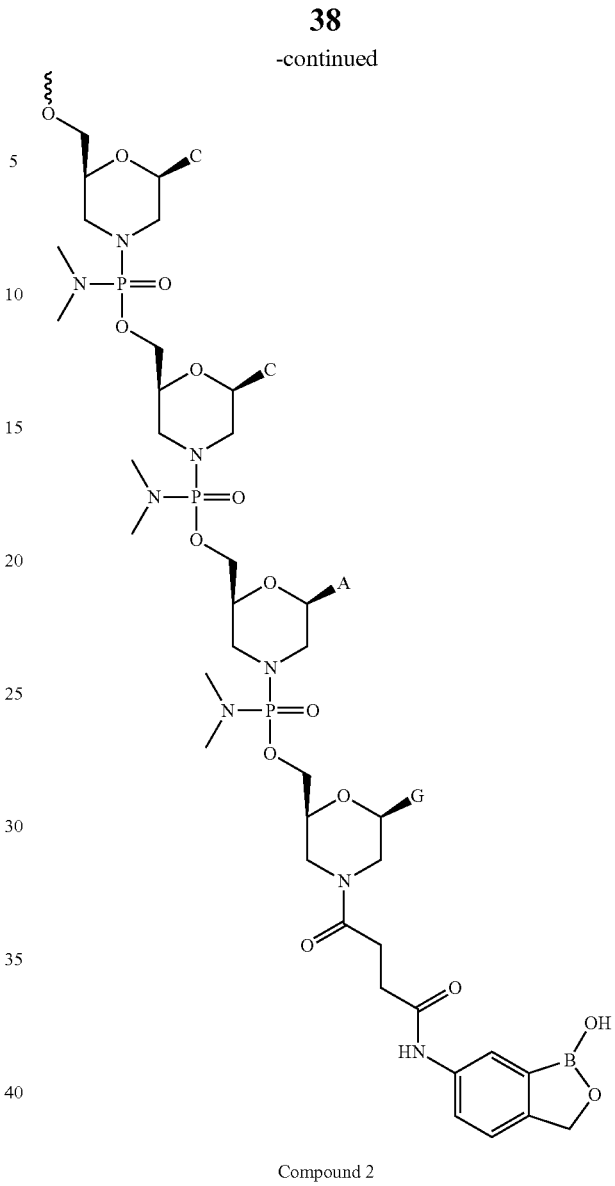

Compound 2

EGFP sequence: 5'-EG3: GCT ATT ACC TTA ACC CAG (SEQ ID NO: 40)

Compound 1, a 5-EG3-PMO (EG3=triethylene glycol) with the EGFP sequence (3'-free base, 30 mg, 4.8 mmol) is dissolved in water (500 mL) at room temperature. To this is added EDC (4 mg, 24 mmol) and N-succinyl-5-aminoboronophthalide (6 mg, 24 mmol), prepared by the method of: WJ Lennarz and HR Snyder, Journal of the American Chemical Society (1960), 82, 2172. The reaction mixture is allowed to stir at room temperature for 18 hours. Reaction progress is monitored by LC-MS (ESI).

Upon completion, water (1.5 mL) is added to the reaction mixture, and this solution is loaded onto an SPE column (2 cm). The column was rinsed water (3×2 mL). The product, Compound 2, is eluted with 45% acetonitrile in water (6 mL). Fractions containing the PMO-BA compound were identified by UV optical density measurement. The product is isolated by lyophilization. Purity and identity are determined by MALDI-MS, LC-MS (ESI), and HPLC (C-18 and/or SAX).

Conjugation of boronic acid or boronic ester moieties to the 5'-end is accomplished in an analogous manner.

Example 2
Preparation of PMO Containing Boronic Acid Intersubunit Linkage
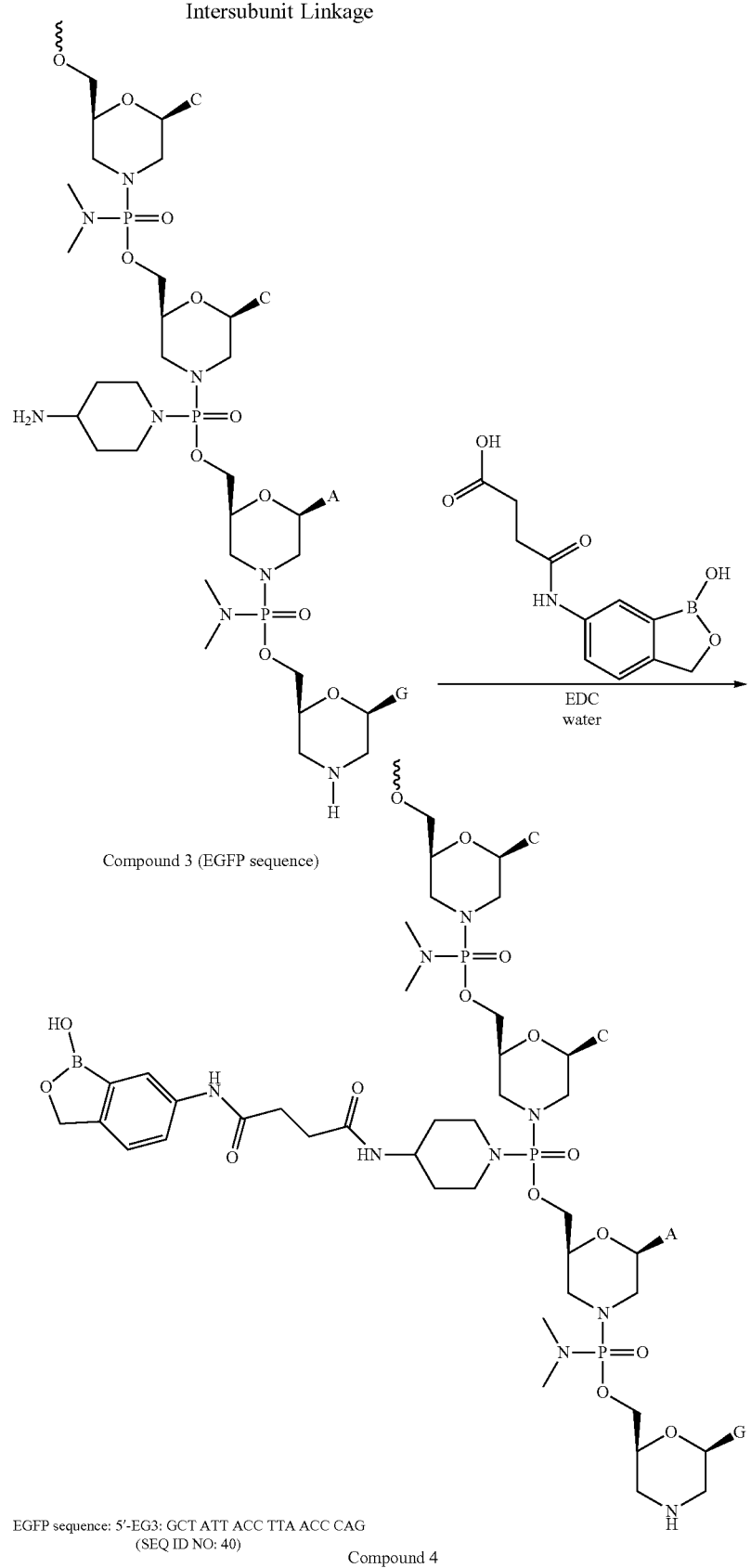
Compound 3 (EGFP sequence)
Compound 4
EGFP sequence: 5'-EG3: GCT ATT ACC TTA ACC CAG
(SEQ ID NO: 40)

Compound 3 (3'-free base, 30 mg, 4.8 mmol) is prepared as described in U.S. Publication No. 2012/0065169 and dissolved in water (500 mL) at room temperature. To this is added EDC (4 mg, 24 mmol) and N-succinyl-5-aminoboronophthalide (6 mg, 24 mmol), prepared by the method of: WJ Lennarz and HR Snyder, Journal of the American Chemical Society (1960), 82, 2172. The reaction mixture is allowed to stir at room temperature for 18 hours. Reaction progress is monitored by LC-MS (ESI).

Upon completion, water (1.5 mL) is added to the reaction mixture, and this solution is loaded onto an SPE column (2 cm). The column was rinsed water (3×2 mL). The product, Compound 4, is eluted with 45% acetonitrile in water (6 mL). Fractions containing the PMO-BA compound are identified by UV optical density measurement. The product is isolated by lyophilization. Purity and identity are determined by MALDI-MS, LC-MS (ESI), and HPLC (C-18 and/or SAX).

The 3'-morpholino may be protected (e.g., trityl) to avoid any unwanted coupling of the boronic acid moiety to the 3'-end.

Example 3

Preparation of PMO Containing Boronic Acid Intersubunit Linkage

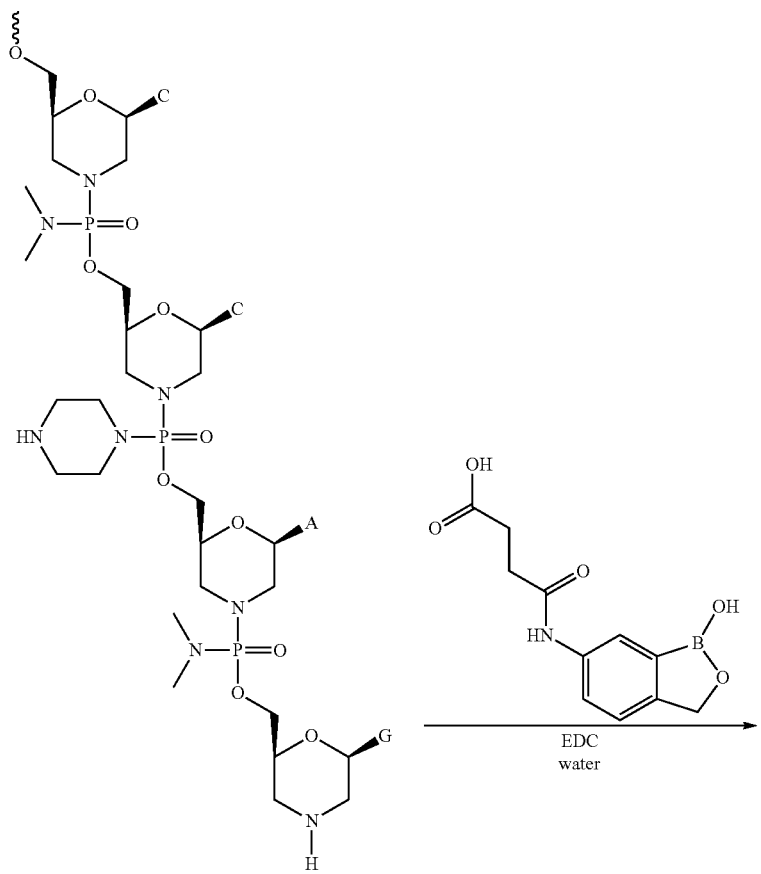

Compound 5 (EGFP sequence)

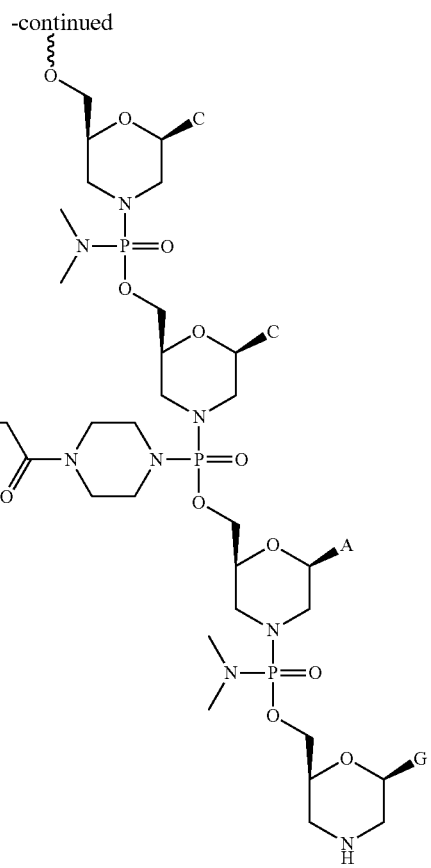

Compound 6

EGFP sequence: 5'-EG3: GCT ATT ACC TTA ACC CAG
(SEQ ID NO: 40)

Compound 5 (3'-free base, 30 mg, 4.8 mmol) is prepared as described in U.S. Pat. No. 7,943,762 and dissolved in water (500 mL) at room temperature. To this is added EDC (4 mg, 24 mmol) and N-succinyl-5-aminoboronophthalide (6 mg, 24 mmol), prepared by the method of: WJ Lennarz and HR Snyder, Journal of the American Chemical Society (1960), 82, 2172. The reaction mixture is allowed to stir at room temperature for 18 hours. Reaction progress is monitored by LC-MS (ESI).

Upon completion, water (1.5 mL) is added to the reaction mixture, and this solution is loaded onto an SPE column (2 cm). The column was rinsed water (3×2 mL). The product, Compound 6, is eluted with 45% acetonitrile in water (6 mL). Fractions containing the PMO-BA compound are identified by UV optical density measurement. The product is isolated by lyophilization. Purity and identity are determined by MALDI-MS, LC-MS (ESI), and HPLC (C-18 and/or SAX).

The 3'-morpholino may be protected (e.g., trityl) to avoid any unwanted coupling of the boronic acid moiety to the 3'-end.

The disclosure of U.S. provisional patent application Ser. No. 61/613,385, filed Mar. 20, 2012, is incorporated herein in its entirety.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An oligonucleotide analogue comprising a backbone, a 3'-terminus and a 5'-terminus, the backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligonucleotide analogue can bind in a sequence-specific manner to a target nucleic acid, wherein at least one of the intersubunit linkages, the 3'-terminus or the 5'-terminus comprises a boronic acid or boronic ester moiety covalently bound thereto, wherein at least one of the morpholino ring structures has the following structure (i):

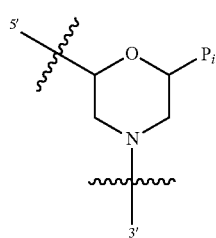

(i)

wherein $P_i$ is, at each occurrence, independently a base-pairing moiety;
the intersubunit linkages have the following structure (III):

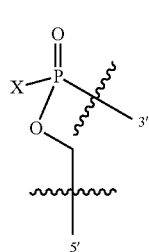

(III)

wherein:
X is, at each occurrence, independently structure (I), structure (II) or —NR$^{10}$R$^{11}$; and
R$^{10}$ and R$^{11}$ are, at each occurrence, independently hydrogen or C$_1$-C$_6$ alkyl, and wherein
the boronic acid or boronic ester moiety has, at each occurrence, independently one of the following structures (I) or (II):

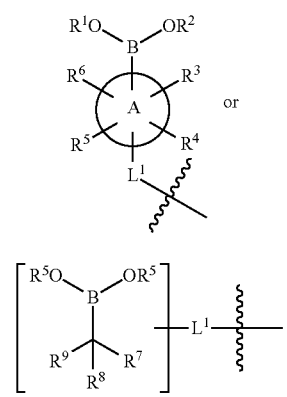

or a pharmaceutically acceptable salt, stereoisomer or tautomer thereof, wherein:
R$^1$ is, at each occurrence, independently H or alkyl;
R$^2$ is H or alkyl, wherein R$^2$ may join with one of R$^3$, R$^4$, R$^5$ or R$^6$ to form a ring;
R$^3$, R$^4$, R$^5$ and R$^6$ are, at each occurrence, independently absent, H, alkyl, aryl, hydroxy, hydroxyalkyl, aminoalkyl, alkoxy, alkoxyalkyl, aryloxy, halo, nitro, cyano, amidyl, amino, alkylamino, aminoalkyl, arylamino, aralkyl, aralklyamino, aralkyloxycarbonylaminyl, alkyloxycarbonylaminyl, aryloxycarbonylaminyl, —CO$_2$H, alkylcarbonyl, arylcarbonyl, aralkylcarbonyl, aminocarbonyl, alkylaminocarbonyl, arylaminocarbonyl, aralkylaminocarbonyl, alkyloxycarbonyl, aryloxycarbonyl, alkyloxyimino or heteroaryl, wherein one of R$^3$, R$^4$, R$^5$ or R$^6$ may join with another one of R$^3$, R$^4$, R$^5$ or R$^6$ to form a carbocyclic or heterocyclic ring, and wherein one of R$^3$, R$^4$, R$^5$ or R$^6$ may join with R$^2$ to form a heterocyclic ring;
R$^7$, R$^8$ and R$^9$ are, at each occurrence, independently alkyl or alkyl amino;
A represents, at each occurrence, independently a 6-membered aryl or heteroaryl ring; and
L$^1$ is, at each occurrence, independently an optional linker up to 18 atoms in length comprising moieties selected from alkyl, aryl, hydroxyl, alkoxy, ether, amino, heteroaryl, phosphorous, alkylamino, guanidinyl, amidinyl, amide, ester, carbonyl, sulfide, disulfide, carbonyl, carbamate, phosphorodiamidate, phosphoroamidate, phosphorothioate, piperazine, phosphodiester and heterocyclyl moieties, wherein

represents a point of covalent attachment of L$^1$ to one of the intersubunit linkages, the 3'-terminus or the 5'-terminus.

2. The oligonucleotide analogue of claim 1, wherein at least one X is structure (I) or (II).

3. The oligonucleotide analogue of claim 1, wherein at least one X is —N(CH$_3$)$_2$.

4. The oligonucleotide analogue of claim 1, wherein each X that is not structure (I) or (II) is —N(CH$_3$)$_2$.

5. The oligonucleotide analogue of claim 1, wherein X in from 1 to 5 of the intersubunit linkages is structure (I) or (II).

6. The oligonucleotide analogue of claim 1, wherein the 3'-terminus is covalently linked to structure (I) or structure (II) and has one of the following structures (IV) or (V):

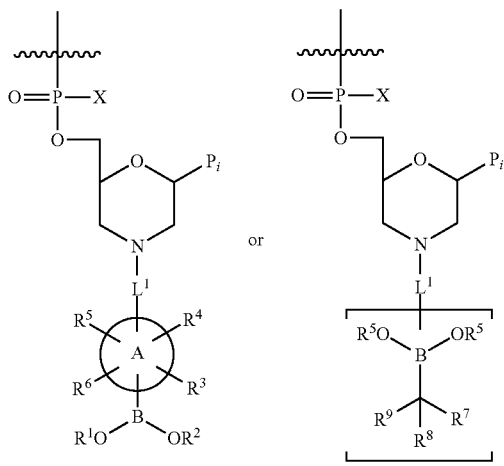

wherein $P_i$ is a base-pairing moiety.

7. The oligonucleotide analogue of claim 1, wherein the 5'-terminus is covalently linked to structure (I) or (II) and has one of the following structures (VI) or (VII):

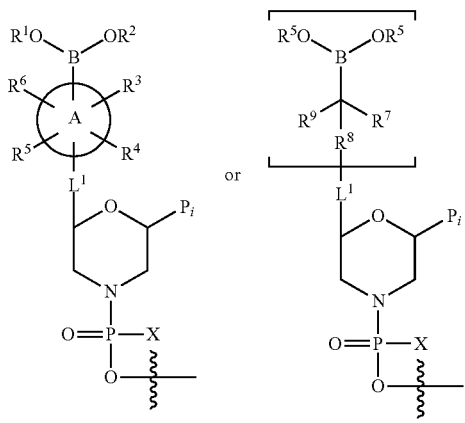

wherein $P_i$ is a base-pairing moiety.

8. The oligonucleotide analogue of claim 1, wherein structure (I) has one of the following structures (Ia), (Ib), (Ic) or (Id):

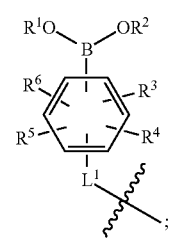
(Ia)

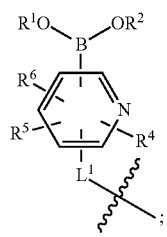
(Ib)

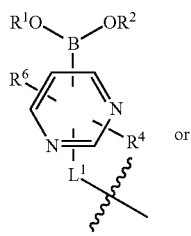
(Ic) or

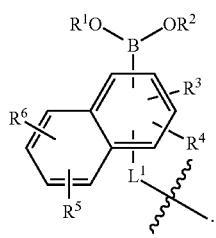
(Id)

9. The oligonucleotide analogue of claim 1, wherein structure (II) has one of the following structures (IIa), (IIb), (IIc) or (IId):

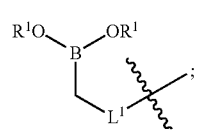
(IIa)

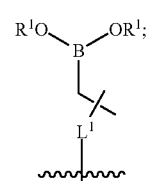
(IIb)

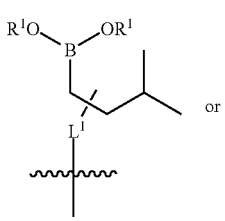
(IIc)

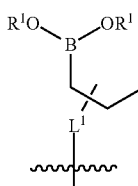 or 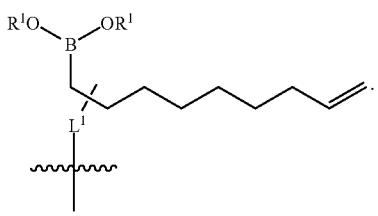
(IId)

10. The oligonucleotide analogue of claim 1, wherein $R^2$ joins with one of $R^3$, $R^4$, $R^5$ or $R^6$ to form a heterocyclic ring.

11. The oligonucleotide analogue of claim 10, wherein structure (I) has the following structure (Ie):

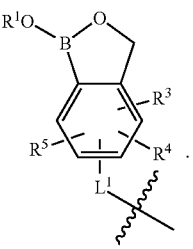
(Ie)

12. The oligonucleotide analogue of claim 1, wherein at least one $R^1$ is H or $R^2$ is H.

13. The oligonucleotide analogue of claim 1, wherein each $R^1$ and $R^2$ is H.

14. The oligonucleotide analogue of claim 1, wherein $R^3$, $R^4$, $R^5$ and $R^6$ are each independently absent, H, hydroxyl, alkyl, hydroxyalkyl, aminoalkyl, alkoxy, aryloxy, halo, nitro, cyano amidyl, amino, alkylamino, aryloxycarbonylaminyl, —$CO_2H$, alkyloxycarbonyl, alkyloxyimino or heteroaryl.

15. The oligonucleotide analogue of claim 1, wherein structure (I) has one of the following structures:

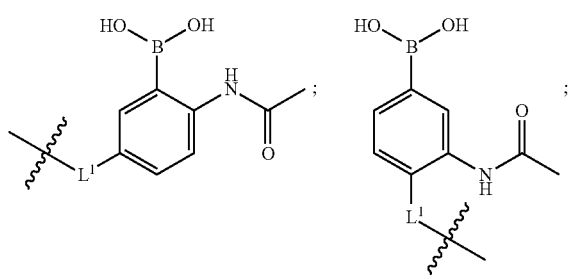
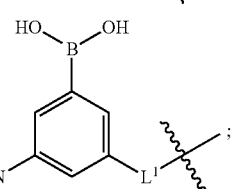
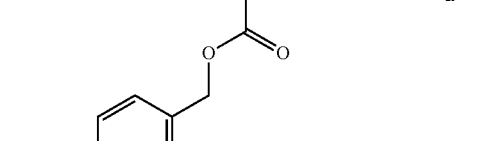
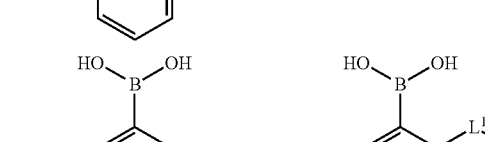
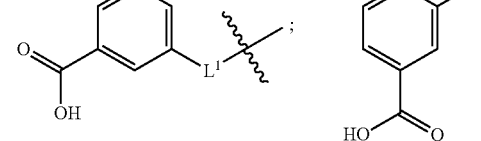
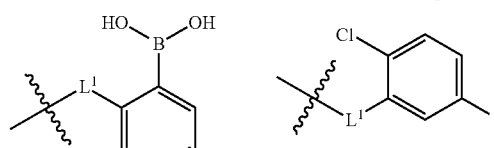
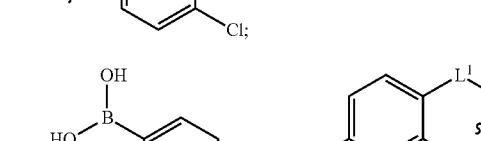
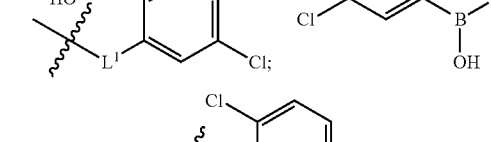
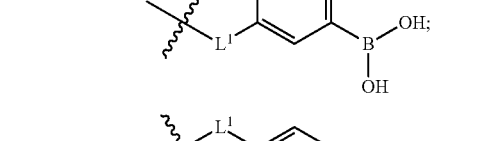
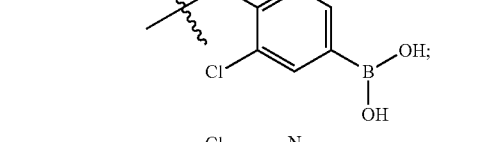
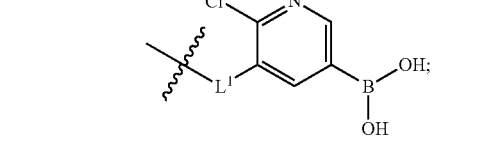
-continued
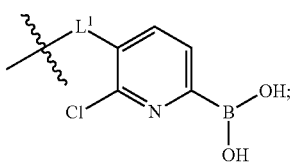
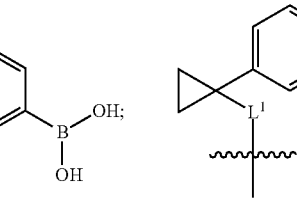
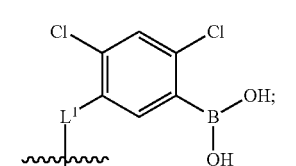
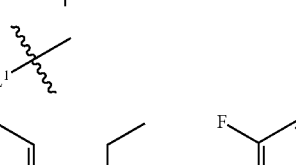
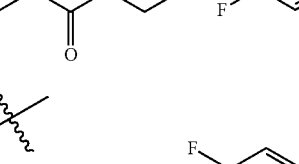
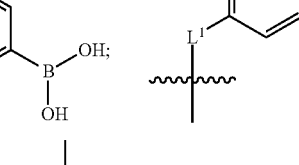
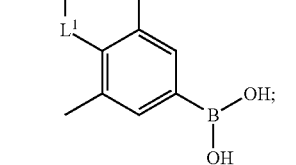

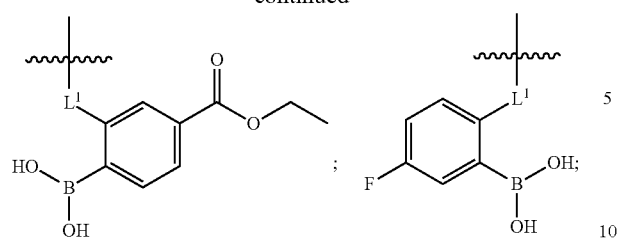
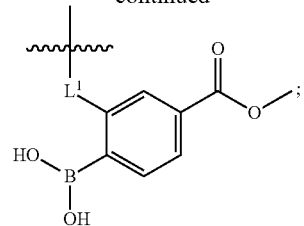
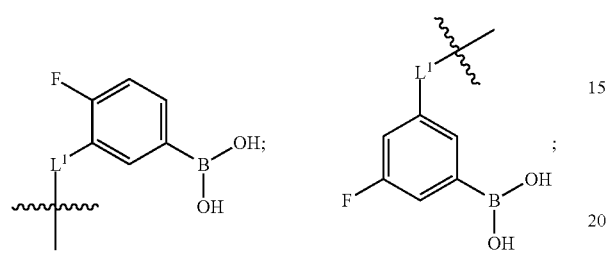
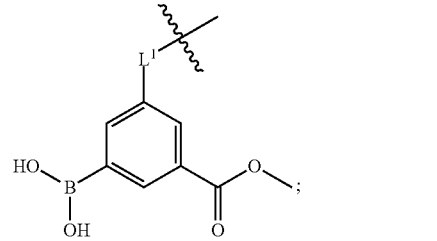
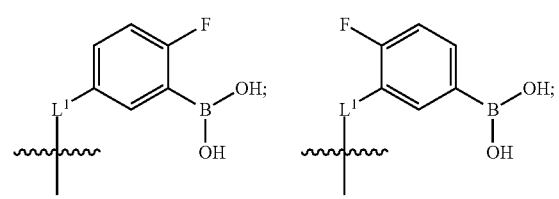
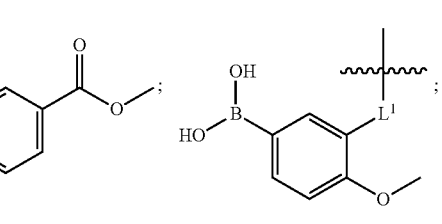
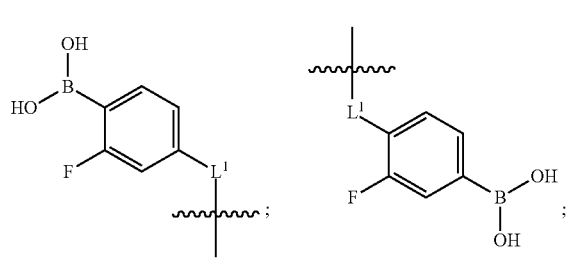
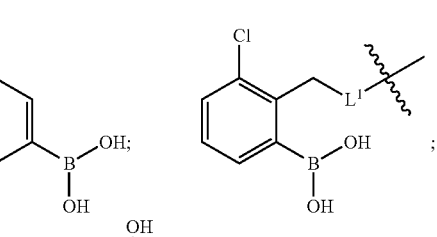
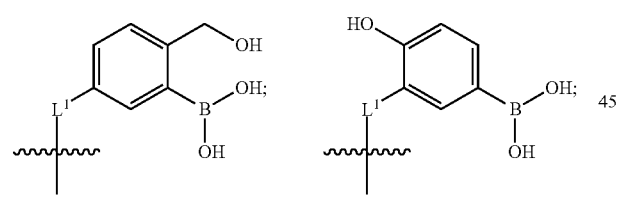
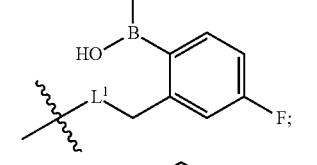
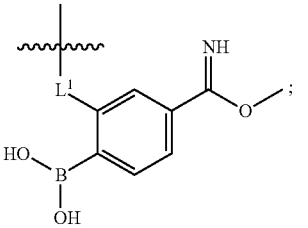
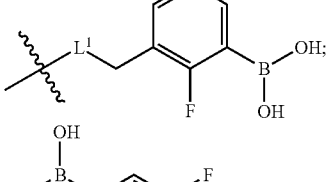
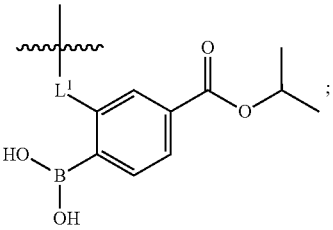
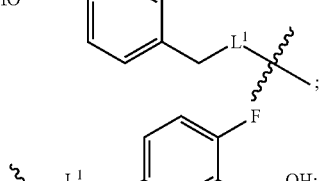
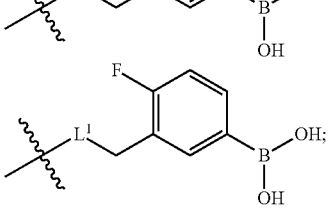

-continued

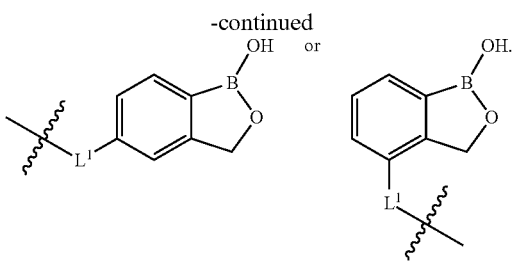

16. The oligonucleotide analogue of claim 1, wherein $L^1$ comprises amide bonds.

17. The oligonucleotide analogue of claim 1, wherein $L^1$ has one of the following structures:

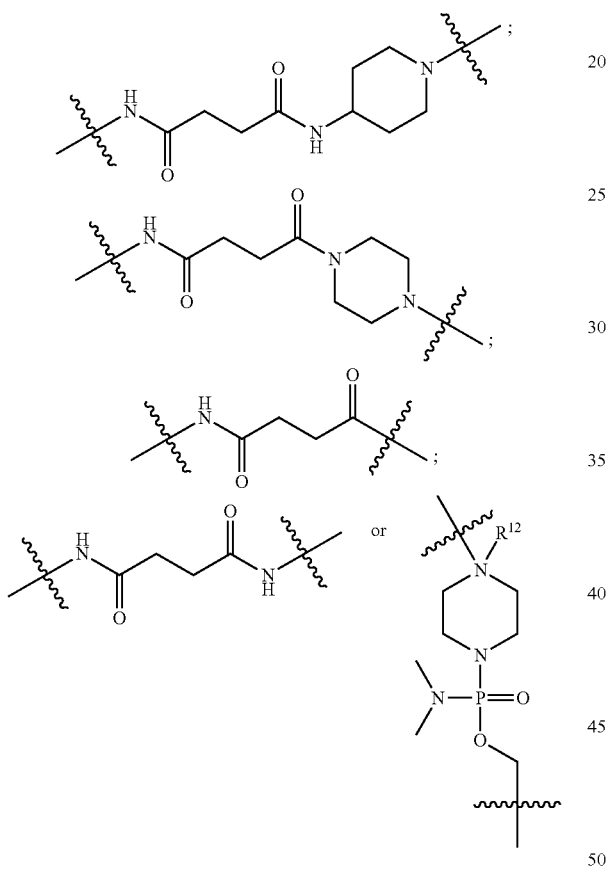

wherein $R^{12}$ is absent, H or $C_1$-$C_6$ alkyl.

18. A composition comprising an oligonucleotide analogue comprising a backbone, a 3'-terminus and a 5'-terminus, the backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligonucleotide analogue can bind in a sequence-specific manner to a target nucleic acid, wherein at least one of the intersubunit linkages, the 3'-terminus or the 5'-terminus comprises a boronic acid or boronic ester moiety covalently bound thereto, and a pharmaceutically acceptable vehicle, wherein at least one of the morpholino ring structures has the following structure (i):

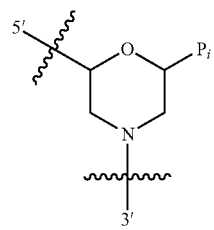

wherein $P_i$ is, at each occurrence, independently a base-pairing moiety;

the intersubunit linkages have the following structure (III):

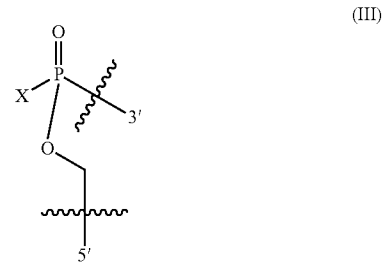

wherein:
X is, at each occurrence, independently structure (I), structure (II) or —$NR^{10}R^{11}$; and
$R^{10}$ and $R^{11}$ are, at each occurrence, independently hydrogen or $C_1$-$C_6$ alkyl, and wherein
the boronic acid or boronic ester moiety has, at each occurrence, independently one of the following structures (I) or (II):

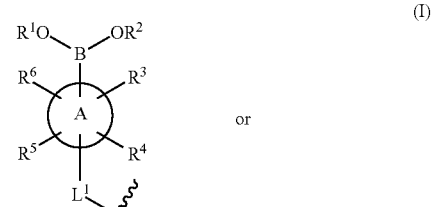

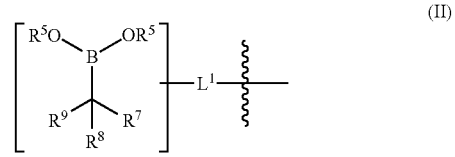

or a pharmaceutically acceptable salt, stereoisomer or tautomer thereof, wherein:
$R^1$ is, at each occurrence, independently H or alkyl;
$R^2$ is H or alkyl, wherein $R^2$ may join with one of $R^3$, $R^4$, $R^5$ or $R^6$ to form a ring;
$R^3$, $R^4$, $R^5$ and $R^6$ are, at each occurrence, independently absent, H, alkyl, aryl, hydroxy, hydroxyalkyl, aminoalkyl, alkoxy, alkoxyalkyl, aryloxy, halo, nitro, cyano, amidyl, amino, alkylamino, aminoalkyl, arylamino, aralkyl, aralklyamino, aralkyloxycarbonylaminyl, alkyloxycarbonylaminyl, aryloxycarbonylaminyl, —CO₂H, alkylcarbonyl, arylcarbonyl, aralkylcarbonyl, aminocarbonyl, alkylaminocarbonyl, arylaminocarbonyl, aralkylaminocarbonyl, alkyloxycarbonyl, aryloxycarbonyl, alkyloxyimino or heteroaryl, wherein one of $R^3$, $R^4$, $R^5$ or $R^6$ may join with another one of $R^3$, $R^4$, $R^5$ or $R^6$ to form a carbocyclic or heterocyclic ring, and wherein one of $R^3$, $R^4$, $R^5$ or $R^6$ may join with $R^2$ to form a heterocyclic ring;

$R^7$, $R^8$ and $R^9$ are, at each occurrence, independently alkyl or alkyl amino;

A represents, at each occurrence, independently a 6-membered aryl or heteroaryl ring; and $L^1$ is, at each occurrence, independently an optional linker up to 18 atoms in length comprising moieties selected from alkyl, aryl, hydroxyl, alkoxy, ether, amino, heteroaryl, phosphorous, alkylamino, guanidinyl, amidinyl, amide, ester, carbonyl, sulfide, disulfide, carbonyl, carbamate, phosphorodiamidate, phosphoroamidate, phosphorothioate, piperazine, phosphodiester and heterocyclyl moieties, wherein

represents a point of covalent attachment of $L^1$ to one of the intersubunit linkages, the 3'-terminus or the 5'-terminus.

19. A method of treating a disease in a subject, the method comprising administering to a subject in need thereof a therapeutically effective amount of the oligonucleotide of claim 1.

20. The method of claim 19, wherein the disease is a neuromuscular disease.

21. The method of claim 20, wherein the neuromuscular disease is Duchenne muscular dystrophy.

22. The oligonucleotide analogue of claim 1, having the formula

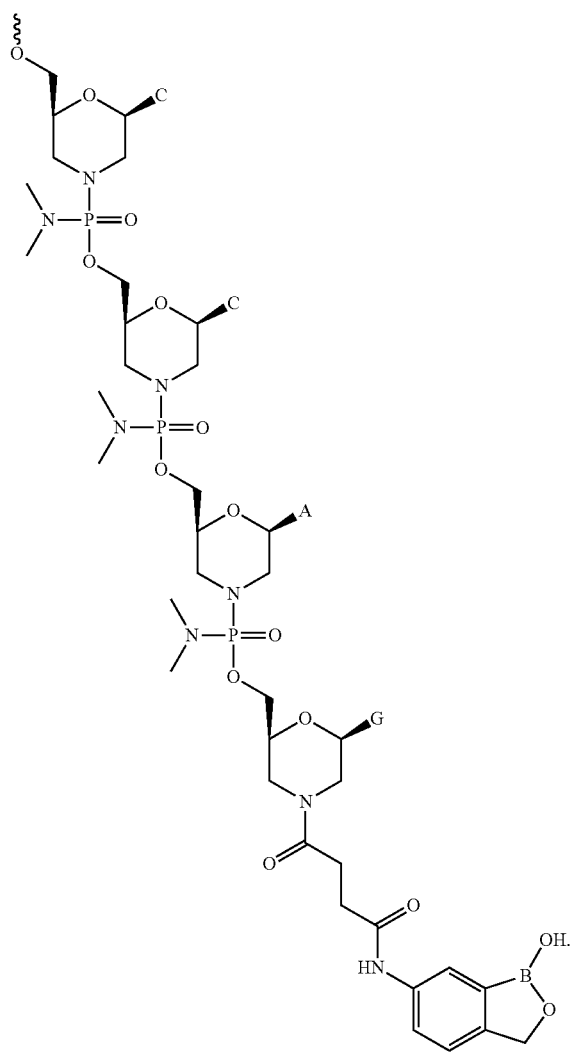

* * * * *